United States Patent
Higuchi et al.

(10) Patent No.: US 8,431,127 B2
(45) Date of Patent: Apr. 30, 2013

(54) METHOD FOR TREATING PRURITUS COMPRISING ADMINISTERING AN NR10 ANTAGONIST

(75) Inventors: Yoshinobu Higuchi, Shizuoka (JP); Keiko Kasutani, Shizuoka (JP); Hidetomo Kitamura, Shizuoka (JP); Masakazu Hasegawa, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/746,229

(22) PCT Filed: Dec. 5, 2008

(86) PCT No.: PCT/JP2008/072142
§ 371 (c)(1),
(2), (4) Date: Aug. 20, 2010

(87) PCT Pub. No.: WO2009/072598
PCT Pub. Date: Jun. 11, 2009

(65) Prior Publication Data
US 2010/0310556 A1     Dec. 9, 2010

(30) Foreign Application Priority Data
Dec. 5, 2007 (JP) ................. 2007-315144

(51) Int. Cl.
*A61K 39/395* (2006.01)
*C07K 16/28* (2006.01)

(52) U.S. Cl.
USPC .............. 424/139.1; 514/18.6; 530/388.1; 530/388.22

(58) Field of Classification Search .............. None
See application file for complete search history.

(56) References Cited

U.S. PATENT DOCUMENTS

| | | | |
|---|---|---|---|
| 6,018,032 A | 1/2000 | Koike et al. | |
| 6,642,360 B2 | 11/2003 | Filvaroff et al. | |
| 6,747,137 B1 | 6/2004 | Weinstock et al. | |
| 6,756,481 B2 | 6/2004 | Chirica et al. | |
| 7,045,595 B2 | 5/2006 | Maeda et al. | |
| 7,250,168 B2 | 7/2007 | Light et al. | |
| 7,411,041 B2 | 8/2008 | Chirica et al. | |
| 7,482,440 B2 | 1/2009 | Maeda et al. | |
| 2003/0082734 A1 | 5/2003 | Dowling et al. | |

(Continued)

FOREIGN PATENT DOCUMENTS

| | | |
|---|---|---|
| AU | 2006/214404 | 8/2006 |
| AU | 2007/249713 | 11/2007 |

(Continued)

OTHER PUBLICATIONS

Itching (Pruritus) by Robert J. MacNeal, May 2009, Merck Manual, on-line at merckmanuals.com, 6 pages as printed.*

(Continued)

*Primary Examiner* — Zachary Howard
(74) *Attorney, Agent, or Firm* — Fish & Richardson P.C.

(57) ABSTRACT

The present inventors isolated clone BM095 from a human antibody phage library, which had a strong growth inhibitory activity in the IL-31-dependent Ba/F3 cell growth assay system. When administered to pruritus model mice, the anti-mouse NR10 neutralizing antibody exhibited a marked symptom-suppressing effect. Thus, it was revealed that anti-NR10 neutralizing antibodies are useful as therapeutic agents for pruritus.

19 Claims, 5 Drawing Sheets

U.S. PATENT DOCUMENTS

| | | | |
|---|---|---|---|
| 2003/0125520 A1 | 7/2003 | Maeda et al. | |
| 2003/0215838 A1 | 11/2003 | Sprecher et al. | |
| 2003/0224487 A1 | 12/2003 | Sprecher et al. | |
| 2004/0142422 A1 | 7/2004 | Sprecher et al. | |
| 2004/0223970 A1 | 11/2004 | Afar et al. | |
| 2006/0106201 A1 | 5/2006 | Maeda et al. | |
| 2006/0166284 A1 | 7/2006 | Light et al. | |
| 2006/0182743 A1 | 8/2006 | Bilsborough | |
| 2007/0160611 A1* | 7/2007 | Yao et al. | 424/145.1 |
| 2007/0203328 A1 | 8/2007 | Maeda et al. | |
| 2008/0019985 A1 | 1/2008 | Light et al. | |
| 2008/0020965 A1 | 1/2008 | Light et al. | |
| 2008/0125579 A1 | 5/2008 | Owens et al. | |
| 2008/0219971 A1 | 9/2008 | Smith et al. | |
| 2009/0023660 A1 | 1/2009 | Maeda et al. | |
| 2009/0029484 A1 | 1/2009 | Maeda et al. | |
| 2009/0105457 A1 | 4/2009 | Maeda et al. | |
| 2009/0105458 A1 | 4/2009 | Maeda et al. | |
| 2009/0105459 A1 | 4/2009 | Maeda et al. | |
| 2009/0111972 A1 | 4/2009 | Maeda et al. | |
| 2010/0016552 A1 | 1/2010 | Maeda et al. | |
| 2010/0055092 A1 | 3/2010 | Hasegawa et al. | |
| 2010/0240096 A1 | 9/2010 | Maeda et al. | |
| 2010/0240145 A1 | 9/2010 | Maeda et al. | |
| 2011/0129459 A1 | 6/2011 | Kuramochi et al. | |
| 2011/0229459 A1 | 9/2011 | Kuramochi et al. | |

FOREIGN PATENT DOCUMENTS

| | | |
|---|---|---|
| AU | 2007/255753 | 12/2007 |
| AU | 2008332271 | 6/2009 |
| CA | 2 708 065 | 6/2009 |
| CA | 2 708 532 | 6/2009 |
| EA | 009026 | 10/2007 |
| EP | 0411946 | 2/1991 |
| EP | 0931646 | 7/1999 |
| EP | 1 088 831 | 4/2001 |
| EP | 1 188 830 | 3/2002 |
| EP | 2 047 863 | 4/2009 |
| EP | 2 236 604 | 10/2010 |
| EP | 2 241 332 | 10/2010 |
| JP | 2005-532045 | 10/2005 |
| WO | WO 94/10354 | 5/1994 |
| WO | WO 94/12215 | 6/1994 |
| WO | WO 95/33059 | 12/1995 |
| WO | WO 96/23071 | 8/1996 |
| WO | WO 97/15663 | 1/1997 |
| WO | WO 97/07215 | 2/1997 |
| WO | WO 97/10354 | 3/1997 |
| WO | WO 97/12037 | 3/1997 |
| WO | WO 99/67290 | 12/1999 |
| WO | WO 00/34317 | 6/2000 |
| WO | WO 00/73451 | 12/2000 |
| WO | WO0075314 A1 | 12/2000 |
| WO | WO0123556 A1 | 4/2001 |
| WO | WO 01/85790 | 11/2001 |
| WO | WO 02/00721 | 1/2002 |
| WO | WO 02/29060 | 4/2002 |
| WO | WO02077230 A1 | 10/2002 |
| WO | WO 03/060090 | 7/2003 |
| WO | WO 03/072740 | 9/2003 |
| WO | WO 2004/003140 | 1/2004 |
| WO | WO 2004/085476 | 10/2004 |
| WO | WO 2004/091543 | 10/2004 |
| WO | WO 03/092602 | 11/2005 |
| WO | WO 2006/004663 | 1/2006 |
| WO | WO 2006/063864 | 6/2006 |
| WO | WO 2006/070286 | 7/2006 |
| WO | WO 2006/081573 | 8/2006 |
| WO | WO 2006/088955 | 8/2006 |
| WO | WO 2006/088956 | 8/2006 |
| WO | WO2006088855 A1 | 8/2006 |
| WO | WO 2006/118959 | 11/2006 |
| WO | WO 2006/119062 | 11/2006 |
| WO | WO 2006/122079 | 11/2006 |
| WO | WO 2007/133816 | 11/2007 |
| WO | WO2007142325 A1 | 12/2007 |
| WO | WO 2008/103432 | 8/2008 |
| WO | WO 2008/132453 | 11/2008 |
| WO | WO 2009/041613 | 4/2009 |
| WO | WO 2009/041621 | 4/2009 |
| WO | WO 2009/041643 | 4/2009 |
| WO | WO 2009/072598 | 6/2009 |
| WO | WO 2009/072604 | 6/2009 |

OTHER PUBLICATIONS

Phillips, A., J Pharm Pharmacology 53: 1169-1174, 2001.*
Vidal et al. 2005. European Journal of Cancer. 41: 2812-2818.*
Pirollo et al, 2008. Cancer Res. 68(5): 1247-1250.*
Zhang et al, 2008. Cytokine & Growth Factor Reviews. 19: 347-356.*
Abbas et al., Cellular and Molecular Immunology, Second edition, W.B. Saunders Co., Philadelphia, pp. 47-48 (1994).
Alexander et al., "Suckling defect in mice lacking the soluble haemopoietin receptor NR6," Current Biology, 9:605-608 (1999).
Baumgartner et al., "The role of the WSXWS equivalent motif in growth hormone receptor function," J. Biol. Chem., 269:29094-29101 (1994).
Bepler et al., "A 1.4-Mb high-resolution physical map and contig of chromosome segment 11p15.5 genes in LOH11A metastasis suppressor region," Genomics, 55:164-175 (1991).
Bilsborough et al., "IL-31 is associated with cutaneous lymphocyte antigen-positive skin homing T cells in patients with atopic dermatitis," J. Allergy Clin. Immunol., 117:418-425 (2006).
Bork et al., "Go hunting in sequence databases but watch out for the traps," Trends Genet., 12:425-427 (1996).
Bork, "Powers and pitfalls in sequence analysis: the 70% hurdle," Genome Res., 10:398-400 (2000).
Castellani et al., "Interleukin-31: A new cytokine involved in inflammation of the skin," Int. J. Immunopathol. Pharmacol., 19:1-4 (2006).
Cioffi et al., "Novel B219/OB receptor isoforms: Possible role of leptin in hematopoiesis and reproduction," Nature Med., 2:585-589 (1996).
Cosman, "A new cytokine receptor superfamily," Trends Biochem. Sci., 15:265-270 (1990).
Cosman, "The hematopoietin receptor superfamily," Cyokine, 5:95-106 (1993).
Dillon et al., "Transgenic mice overexpressing a novel cytokine (IL-31) develop a severe pruritic skin phenotype resembling atopic dermatitis," Eur. Cytokine Netw., 14(suppl. 3):81 (#223) (2003).
Diveau et al., "Predominant expression of the long isoform of the GP130-like (GPL) receptor is required for interleukin-31 signaling," Eur. Cytokine Netw., 15:291-302 (2004).
Donaldson et al., "The murine IL-13 receptor α2: Molecular cloning, characterization, and comparison with murine IL-13 receptor α2," J. Immunol., 161:2317-24 (1998).
EMBL Accession No. AI123586 dated Sep. 8, 1998.
EMBL Accession No. W16834 dated May 4, 1996.
Gainsford et al., "Leptin can induce proliferation, differentiation, and functional activation of hemopoietic cells," Proc. Natl. Acad. Sci. USA, 93:14564-68 (1996).
Genbank Accession No. AAM44229 (hIL-23R), Oct. 19, 2004.
GenBank Accession No. AF102051, Jan. 28, 1999.
Genbank Accession No. AQ022781, Jun. 16, 1998.
Genbank Accession No. AY499342, Jul. 10, 2004.
Genbank Accession No. NM_139017, Aug. 3, 2005.
Hibi et al., "Molecular cloning and expression of an IL-6 signal transducer, gp130," Cell, 63:1149-57 (1990).
Hilton et al., "Cloning and characterization of a binding subunit of the interleukin 13 receptor that is also a component of the interleukin 4 receptor," Proc. Natl. Acad. Sci. USA, 93:497-501 (1996).
Hilton et al., "Cloning of a murine IL-11 receptor α-chain; requirement for gp130 for high affinity binding and signal transduction," EMBO J., 13:4765-75 (1994).
Irnaten et al., "Prediction of epitopes and production of monoclonal antibodies against gastric H,K-ATPase," Protein Eng., 11:949-955 (1998).
Jabbour et al., "Expression of functional prolactin receptors in non-pregnant human endometrium: janus kinase-2, signal transducer and activator of transcription-1 (STAT1), and STAT5 proteins are phosphorylated after stimulation with prolactin," J. Clin. Endocrinol. Metab., 83:2545-53 (1998).

Kernebeck et al., "The signal transducer gp130: solution structure of the carboxy-terminal domain of the cytokine receptor homology region," Protein Sci., 8:5-12 (1999).

Mahairas et al., "Sequence-tagged connectors: A sequence approach to mapping and scanning the human genome," Proc. Natl. Acad. Sci. USA, 96:9739-44 (1999).

Matsuno et al., "Treatment of rheumatoid synovitis with anti-reshaping human interleukin-6 receptor monoclonal antibody," Arthr. Rheum., 41:2014-21 (1998).

Matthews et al., "A receptor tyrosine kinase specific to hematopoietic stem and progenitor cell-enriched populations," Cell, 65:1143-52 (1991).

Meinkoth and Wahl, "Hybridization of Nucleic Acids Immobilized on Solid Supports," Anal. Biochem., 138:267-284 (1984).

Miyajima et al., "Cytokine receptors and signal transduction," Annu. Rev. Immunol., 10:295-331, (1992).

Miyazaki et al., "The integrity of the conserved 'WS motif' common to IL-2 and other cytokine receptors is essential for ligand binding and signal transduction," EMBO J., 10:3191-97 (1991).

Murakami et al., "Critical cytoplasmic region of the interleukin 6 signal transducer gp130 is conserved in the cytokine receptor family," Proc. Natl. Acad. Sci., 88:11349-53 (1991).

Nagata et al., "Novel IL-31 cytokine," Rheumatology, 35:282-286 (2006).

Nishimoto et al., "Improvement in Castleman's disease by humanized anti-interleukin-6 receptor antibody therapy," Blood, 95:56-61 (2001).

Nishimoto et al., "Toxicity, pharmacokinetics, and dose-finding study of repetitive treatment with the humanized anti-interleukin 6 receptor antibody MRA in rheumatoid arthritis. Phase I/II clinical study," J. Rheumatol., 30:1426-35 (2003).

Oppmann et al., "Novel p19 protein engages IL-12p40 to form a cytokine, IL-23, with biological activities similar as well as distinct from IL-12," Immunity, 13:715-725 (2000).

Ozaki et al., "Cytokine receptor pleiotropy and redundancy," J. Biol. Chem., 277:29355-56 (2002).

Parham, et al., "A receptor for the heterodimeric cytokine IL-23 is composed of IL-12Rβ1 and a novel cytokine receptor subunit, IL-23R," J. Immunol., 168:5699-5708 (2002).

Phillips, "The challenge of gene therapy and DNA delivery," J. Pharm. Pharmacol., 53:1169-74 (2001).

Pirollo et al., "Targeted delivery of small interfering RNA: approaching effective cancer therapies," Cancer Res., 68:1247-50 (2008).

Robb et al., "Structural analysis of the gene encoding the murine interleukin-11 receptor α-chain and a related locus," J. Biol. Chem., 271:13754-61 (1996).

Saito et al., "Molecular closing of a murine IL-6 receptor-associated signal transducer, gp130, and its regulated expression in vivo," J. Immunol., 148:4066-71 (1992).

Sato et al., "Reshaping a human antibody to inhibit the interleukin 6-dependent tumor cell growth," Cancer Res., 53:851-856 (1993).

Simard et al., "Ontogeny of growth hormone receptors in human tissues: an immunohistochemical study," J. Clin. Endocrinol. Metab., 81:3097-3102 (1996).

Sonkoly et al., "IL-31: a new link between T cells and pruritus in atopic skin inflammation," J. Allergy Clin. Immunol , 117:411-417 (2006).

Vaughan et al., "Human antibodies by design," Nature Biotechnol., 16:535-539 (1998).

Vidal et al., "Making sense of antisense," Eur. J. Cancer, 41:2812-18 (2005).

Wells et al., "Hematopoietic receptor complexes," Annu. Rev. Biochem., 65:609-634 (1996).

Wells, "Additivity of mutational effects in proteins," Biochemistry, 29:8509-17 (1990).

USPTO Restriction Requirement in U.S. Appl. No. 12/303,684, mailed Aug. 23, 2010, 7 pages.

Fish & Richardson P.C. Amendment and Response to Restriction Requirement dated Aug. 23, 2010 in U.S. Appl. No. 12/303,684, filed Sep. 15, 2010, 3 pages.

USPTO Non-Final Office Action in U.S. Appl. No. 12/303,684, mailed Oct. 14, 2010, 18 pages.

International Search Report for App. Ser. No. PCT/JP2007/061625, mailed Sep. 18, 2007, 2 pages.

Bilsborough, "IL-31 is associated with cutaneous lymphocyte antigen-positive skin homing T cells in patients with atopic dermatitis," J. Allergy Clin. Immunol., 117:418-425 (2006).

Dillon et al., "Interleukin 31, a cytokine produced by activated T cells, induces dermatitis in mice," Nat. Immunol., 5:752-760 (2004).

Diveu et al., "GPL, a novel cytokine receptor related to GP130 and leukemia inhibitory factor receptor," J. Biol. Chem., 278:49850-59 (2003).

Ghilardi et al., "A novel type I cytokine receptor is expressed on monocytes, signals proliferation, and activates STAT-3 and STAT-5," J. Biol. Chem., 277:16831-36 (2002).

Higa et al., "Administration of anti-interleukin 18 antibody fails to inhibit development of dermatitis in atopic dermatitis-model mice NC/Nga," Br. J. Dermatol., 149:39-45 (2003).

International Search Report for App. Ser. No. PCT/JP2008/072142, mailed Jan. 6, 2009, 2 pages.

International Preliminary Report on Patentability for App. Ser. No. PCT/JP2008/072142, dated Aug. 10, 2010, 5 pages.

Levin et al., "Optimizing the affinity and specificity of proteins with molecular display," Mol. Biosyst., 2(1):49-57 (2006) (Epub Nov. 8, 2005).

Onda et al., "Lowering the isoelectric point of the Fv portion of recombinant immunotoxins leads to decreased nonspecific animal toxicity without affecting antitumor activity," Cancer Res., 61(13):5070-5077 (2001).

Fish & Richardson P.C., Amendment in Reply to Final Office Action dated Oct. 14, 2011 in U.S. Appl. No. 12/303,684, filed Jun. 12, 2012, 20 pages.

USPTO Interview Summary in U.S. Appl. No. 12/303,684, mailed Jun. 14, 2012, 4 pages.

Chirino et al., "Minimizing the immunogenicity of protein therapeutics," Drug Discov. Today, 9(2):82-90 (2004).

Ewert et al., "Stability improvement of antibodies for extracellular and intracellular applications: CDR grafting to stable frameworks and structure-based framework engineering," Methods, 34:184-199 (2004).

Hanes et al., "Picomolar affinity antibodies from a fully synthetic naive library selected and evolved by ribosome display," Nat. Biotechnol., 18(12):1287-1292 (2000).

Neis et al., "Enhanced expression levels of IL-31 correlate with IL-4 and IL-13 in atopic and allergic contact dermatitis," J. Allergy Clin. Immunol., 118(4):930-937 (2006).

Raap et al., "Correlation of IL-31 serum levels with severity of atopic dermatitis," J. Allergy Clin. Immunol., 122(2):421-423 (2008).

Tan et al., "Engineering the isoelectric point of a renal cell carcinoma targeting antibody greatly enhances scFv solubility," Immunotechnology, 4(2):107-114 (1998).

Yagi et al., "Interleukin-31 stimulates production of inflammatory mediators from human colonic subepithelial myofibroblasts," Int. J. Mol. Med., 19(6):941-946 (2007).

Benjamini et al., Immunology: A Short Course, 2nd Edition, p. 40 only (1991).

Cork et al., "Epidermal barrier dysfunction in atopic dermatitis," J. Invest. Dermatol., 129:1892-1908 (2009).

Grimstad et al., "Anti-interleukin-31-antibodies ameliorate scratching behaviour in NC/Nga mice: a model of atopic dermatitis," Exp. Dermatol., 18:35-43 (2009).

Fish & Richardson P.C., Amendment in Reply to Office Action dated Oct. 14, 2010 in U.S. Appl. No. 12/303,684, filed Apr. 12, 2011, 11 pages.

USPTO Restriction Requirement in U.S. Appl. No. 12/303,684, mailed Jun. 21, 2011, 5 pages.

Fish & Richardson P.C., Response to Restriction Requirement dated Jun. 21, 2011 in U.S. Appl. No. 12/303,684, filed Jul. 12, 2011, 2 pages.

USPTO Final Office Action in U.S. Appl. No. 12/303,684, mailed Oct. 14, 2011, 17 pages.

International Preliminary Report on Patentability for App. Ser. No. PCT/JP2007/061625, dated Jan. 13, 2009, 11 pages.

European Search Report for App. Ser. No. EP 07 74 4945, dated Oct. 29, 2009, 4 pages.

International Preliminary Report on Patentability for App. Ser. No. PCT/JP2009/070376, dated Jul. 5, 2011, 11 pages.

European Search Report for App. Ser. No. EP 11 169 972, dated Aug. 29, 2011, 11 pages.

R&D Systems (R&D Systems, Anti-human IL-31 RA Antibody, Catalog #AF2769, Oct. 2008), 1 page.

USPTO Restriction Requirement in U.S. Appl. No. 12/745,781, dated Jul. 30, 2012, 9 pages.

Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell. Biol.*, 111:2129-2138 (1990).

Lazar et al., "Transforming growth factor alpha: mutation of aspartic acid 47 and leucine 48 results in different biological activities," *Mol. Cell. Biol.*, 8:1247-1252 (1988).

Padlan et al., "Identification of specificity-determining residues in antibodies," *FASEB J.*, 9:133-139 (1995).

R&D Systems (R&D Systems, Biotinylated Anti-human IL-31 RA Antibody, Catalog #BAF2769, Nov. 2005), 1 page.

USPTO Restriction Requirement in U.S. Appl. No. 12/745,781, dated Sep. 4, 2012, 10 pages.

Fish & Richardson P.C., Response to Restriction Requirement dated Sep. 4, 2012 in U.S. Appl. No. 12/745,781, filed on Sep. 21, 2012, 176 pages.

USPTO Non-Final Office Action in U.S. Appl. No. 12/745,781, dated Oct. 18, 2012, 21 pages.

USPTO Restriction Requirement in U.S. Appl. No. 12/809,138, dated Dec. 13, 2012, 8 pages.

Krauss et al., "Impact of antibody framework residue VH-71 on the stability of a humanised anti-MUC1 scFv and derived immunoenzyme," *Br. J. Cancer*, 90:1863-70 (2004).

Marks et al., "By-passing immunization: building high affinity human antibodies by chain shuffling," *Biotechnology (N.Y.)*, 10(7):779-83 (1992).

Ohno et al., "Antigen-binding specificities of antibodies are primarily determined by seven residues of VH," *Proc. Natl. Acad. Sci. U.S.A.*, 82(9):2945-9 (1985).

Roitt et al., *Immunology*, M., Mir, 110, 150, 537-9 (2000) (with English translations).

Rudikoff et al., "Single amino acid substitution altering antigen-binding specificity," *Proc. Natl. Acad. Sci. U.S.A.*, 79(6):1979-83 (1982).

Singer et al., Genes & Genomes (Russian translation from English) 1:63 (1998) (with English translation).

Yang et al., "CDR walking mutagenesis for the affinity maturation of a potent human anti-HIV-1 antibody into the picomolar range," *J. Mol. Biol.*, 254(3):392-403 (1995).

\* cited by examiner

METHOD FOR TREATING PRURITUS COMPRISING ADMINISTERING AN NR10 ANTAGONIST

CROSS-REFERENCE TO RELATED APPLICATIONS

This application is the National Stage of International Application Serial No. PCT/JP2008/072142, filed on Dec. 5, 2008, which claims the benefit of Japanese Application Serial No. 2007-315144, filed on Dec. 5, 2007.

TECHNICAL FIELD

The present invention relates to agents for treating or preventing pruritus.

BACKGROUND ART

Many cytokines are known as humoral factors involved in the growth and differentiation of various types of cells, or in the activation of differentiated mature cell functions. Cytokine-stimulated cells produce different types of cytokines, thereby forming networks of multiple cytokines in the body. Biological homeostasis is maintained by a delicate balance of the mutual regulation between cytokines in these networks. Many inflammatory diseases are thought to result from a failure of such cytokine networks. Thus, monoclonal antibody-based anti-cytokine therapy is drawing much attention. For example, anti-TNF antibodies and anti-IL-6 receptor antibodies have been demonstrated to be highly effective clinically. On the other hand, there are many examples of failure where no therapeutic effects were produced when a single cytokine, such as IL-4, was blocked alone, due to the activation of compensatory pathways in actual pathological conditions.

The present inventors succeeded in isolating a novel cytokine receptor NR10 that was highly homologous to gp130, a receptor for IL-6 signal transduction (Patent Document 1). NR10 forms a heterodimer with oncostatin M receptor (OSMR) and functions as an IL-31 receptor (Non-patent Document 1). NR-10 is also known as glm-r (Non-patent Document 2), GPL (Non-patent Document 3), IL-31RA (Non-patent Document 4), and such. It has also been reported that transgenic mice overexpressing IL-31 spontaneously develop pruritic dermatitis (Non-patent Document 4).

However, it cannot be asserted that forced cytokine expression in mice or a high concentration of blood cytokine in pathological mice are actual causes of the disease. It is totally unclear whether signal blockage by an antibody produces a therapeutic effect. For example, transgenic mice in which IL-18 is overexpressed in keratinocytes develop pruritic dermatitis. In spontaneous atopic dermatitis model mice NC/Nga, the blood concentration of IL-18 increases with advancement of the pathological conditions. From these findings, the overexpression of IL-18 was presumed to be a cause of the disease. Actually, however, the administration of a neutralizing antibody exhibited no therapeutic effect (Non-patent Document 5).

Thus, the inhibition of cytokine function does not necessarily produce a therapeutic effect in diseases with elevated cytokine expression. It is thus difficult to predict from the expression level of a cytokine what disease the inhibition of the cytokine produces a therapeutic effect on. Therefore, it is important to identify diseases on which the inhibition of signaling of a target cytokine actually produces a therapeutic effect.

Prior art documents of the present invention are described below:

Patent Document 1: WO00/75314
Non-patent Document 1: IL-31 is associated with cutaneous lymphocyte antigen-positive skin homing T cells in patients with atopic dermatitis., J Allergy Clin Immunol. 2006 February; 117(2):418-25.
Non-patent Document 2: A novel type I cytokine receptor is expressed on monocytes, signals proliferation, and activates STAT-3 and STAT-5. J Biol Chem 277, 16831-6, 2002
Non-patent Document 3: GPL, a novel cytokine receptor related to GP130 and leukemia inhibitory factor receptor. J Biol Chem 278, 49850-9, 2003
Non-patent Document 4: Interleukin 31, a cytokine produced by activated T cells, induces dermatitis in mice. Nat Immunol 5, 752-60, 2004
Non-patent Document 5: Administration of anti-interleukin 18 antibody fails to inhibit development of dermatitis in atopic dermatitis-model mice NC/Nga., British Journal of Dermatology 149: 39-45, 2003

DISCLOSURE OF THE INVENTION

Problems to be Solved by the Invention

The present invention was achieved in view of the circumstances described above. An objective of the present invention is to provide agents for treating or preventing pruritus.

Means for Solving the Problems

The present inventors conducted dedicated studies to achieve the objective described above. The present inventors discovered that NR10 antagonists such as neutralizing antibodies against NR10 are useful as therapeutic or preventive agents for pruritus, thereby completing the present invention.

The present invention relates to agents for treating or preventing pruritus. More specifically, the present invention provides:

[1] a preventive or therapeutic agent for pruritus, which comprises an NR10 antagonist as an active ingredient;
[2] the preventive or therapeutic agent of [1], wherein the NR10 antagonist is an antibody having a neutralizing activity against NR10;
[3] the preventive or therapeutic agent of [2], wherein the antibody is a monoclonal antibody;
[4] the preventive or therapeutic agent of [3], wherein the antibody is a monoclonal antibody having a neutralizing activity against human NR10;
[5] the preventive or therapeutic agent of any one of [2] to [4], wherein the antibody is a recombinant antibody; and
[6] the preventive or therapeutic agent of any one of [2] to [5], wherein the antibody is a chimeric, humanized, or human antibody.

MODE FOR CARRYING OUT THE INVENTION

Figure 1:
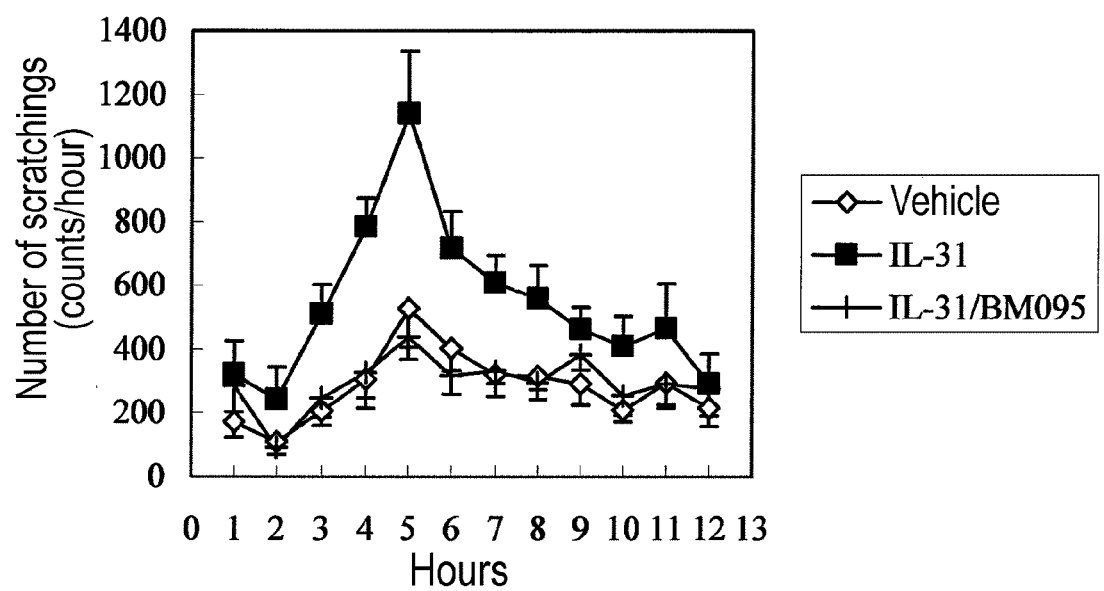
FIG. 1 is a graph showing the assessment of IL-31-induced scratching behavior. Mean±standard error.

NR10 is a protein that forms a heterodimer with oncostatin M receptor (OSMR) and functions as an IL-31 receptor. NR10 is also known as glm-r (J Biol Chem 277, 16831-6, 2002), GPL (J Biol Chem 278, 49850-9, 2003), IL-31RA (Nat Immunol 5, 752-60, 2004), and such. Thus, NR10 in the present invention also includes proteins called by these names.

NR10 in the present invention includes those derived from humans, mice, and other mammals. Preferred NR10 includes, without particular limitation, those derived from humans and mice. There are multiple known splicing variants of human-derived NR10 (WO 00/075314). Of the above-described splicing variants, NR10.1 consists of 662 amino acids and contains a transmembrane domain. NR10.2 is a soluble receptor-like protein consisting of 252 amino acids without the transmembrane domain. Meanwhile, known NR10 splicing variants that function as transmembrane receptor proteins include NR10.3 and IL-31RAv3. The human NR10 of the present invention is not particularly limited, as long as it forms a heterodimer with oncostatin M receptor (OSMR) and functions as an IL-31 receptor. Preferred NR10 includes NR10.3 (also referred to as ILRAv4 (Nat Immunol 5, 752-60, 2004)) and IL-31RAv3. NR10.3 (IL-31RAv4) consists of 662 amino acids (WO 00/075314; Nat Immunol 5, 752-60, 2004) and IL-31RAv3 consists of 732 amino acids (GenBank Accession No: NM_139017). The amino acid sequence of IL-31RAv4 is shown in SEQ ID NO: 6, and the amino acid sequence of IL-31RAv3 is shown in SEQ ID NO: 7. Meanwhile, mouse-derived NR10 includes proteins comprising the amino acid sequence of SEQ ID NO: 5.

In the present invention, the term NR10 antagonist refers to a substance that blocks intracellular signaling mediated by NR10 activation through binding to NR10 and thus causes loss or suppression of the biological activity of the cells. The biological activity includes, but is not limited to, for example, activities of inducing or suppressing the production of a bioactive substance (for example, chemokines, inflammatory cytokines, and such), activities of promoting or suppressing the secretion of a bioactive substance, growth activities, growth-inducing activities, survival activities, differentiation activities, differentiation-inducing activities, transcriptional activities, membrane transport activities, binding activities, proteolytic activities, phosphorylation/dephosphorylation activities, oxidation-reduction activities, transfer activities, nucleolytic activities, dehydration activities, cell death-inducing activities, and apoptosis-inducing activities.

The presence of the antagonistic activity can be determined by methods known to those skilled in the art. For example, a test compound can be contacted with NR10 expressed on cell surface in the presence of a ligand to determine whether the intracellular signal transduction that serves an indicator for NR10 activation occurs or not. This determination can be performed, for example, according to the method described in the reference "Dillon S R, et al., Interleukin 31, a cytokine produced by activated T cells, induces dermatitis in mice. Nat. Immunol. 2004 July; 5(7):752-60". Compounds that inhibit the intracellular signaling responding to the ligand stimulation are considered to be NR10 antagonists.

The antagonists of the present invention may be naturally-occurring or artificial compounds. Known antagonists can be used in the present invention. It is also possible to use novel compounds that have been determined to have an antagonistic activity by the methods described above.

An embodiment of the NR10 antagonist of the present invention includes antibodies that bind to NR10. Such antibodies that bind to NR10 are not particularly limited; however, antibodies that specifically bind to NR10 are preferred. A preferred embodiment of the antibodies that bind to NR10 includes antibodies having a neutralizing activity against NR10. In the present invention, the "antibody having a neutralizing activity against NR10" refers to an antibody having an activity of suppressing a biological activity based on NR10. In the present invention, "antibodies having a neutralizing activity against NR10" may be polyclonal or monoclonal antibodies; however, in a preferred embodiment, the antibodies are monoclonal antibodies.

The antibodies of the present invention are not particularly limited as long as they bind to NR10, and include recombinant antibodies such as chimeric antibodies, humanized antibodies, and human antibodies. The chimeric antibodies contain, for example, the heavy and light chain constant regions of a human antibody, and the heavy and light chain variable regions of a non-human mammal, such as mouse. The chimeric antibodies can be produced by known methods. For example, the antibodies can be produced by cloning an antibody gene from hybridomas, inserting it into an appropriate vector, and introducing the construct into hosts (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs of the antibody variable regions (V regions) are synthesized from mRNA of hybridomas using reverse transcriptase. Once DNAs encoding the V regions of an antibody of interest are obtained, these are linked with DNAs encoding the constant regions (C regions) of a desired human antibody. The resulting constructs are inserted into expression vectors. Alternatively, the DNAs encoding the antibody V regions may be inserted into expression vectors comprising DNAs encoding the C regions of a human antibody. The DNAs are inserted into expression vectors so that they are expressed under the regulation of the expression regulatory regions, for example, enhancers and promoters. In the next step, host cells can be transformed with the expression vectors to allow expression of chimeric antibodies.

Humanized antibodies are also referred to as reshaped human antibodies, and they are prepared by transferring the complementarity determining regions (CDRs) of an antibody derived from a non-human mammal such as a mouse, to the CDRs of a human antibody. General genetic recombination techniques for their preparation are also known. Specifically, a DNA sequence designed such that the CDRs of the mouse antibody are linked with framework regions (FRs) of human antibody is synthesized by PCR using, as primers, several oligonucleotides that have portions overlapping the ends of both CDRs and FRs. The resulting DNA is then ligated to a DNA encoding a human antibody constant region, inserted into an expression vector, and introduced into a host to produce the antibody (see European Patent Application Publication No. EP 239400 and International Patent Application Publication No. WO 96/02576) FRs to be linked via CDRs are selected so that the CDRs form a favorable antigen-binding site. If needed, amino acids in the framework regions of antibody variable region may be substituted so that the CDRs of the reshaped human antibody form a proper antigen-binding site (Sato, K. et al., Cancer Res. (1993) 53, 851-856).

Methods for obtaining human antibodies are also known. For example, desired human antibodies with antigen-binding activity can be obtained by sensitizing human lymphocytes with antigens of interest or cells expressing antigens of interest in vitro; and fusing the sensitized lymphocytes with human myeloma cells such as U266 (see Japanese Patent Application Kokoku Publication No. (JP-B) H01-59878 (examined, approved Japanese patent application published for opposition)). Alternatively, the desired human antibody can also be obtained by immunizing a transgenic animal having an entire repertoire of human antibody genes with a desired antigen (see International Patent Application Publication Nos. WO 93/12227, WO 92/03918, WO 94/02602, WO 94/25585, WO 96/34096, and WO 96/33735).

Furthermore, techniques to obtain human antibodies by panning with a human antibody phage library are known. For example, the variable region of a human antibody is expressed as a single chain antibody (scFv) on the surface of a phage, using a phage display method, and phages that bind to the antigen can be selected. By analyzing the genes of selected phages, the DNA sequences encoding the variable regions of human antibodies that bind to the antigen can be determined. If the DNA sequences of scFvs that bind to the antigen are identified, appropriate expression vectors comprising these sequences can be constructed to obtain human antibodies. Such methods are well known. Reference can be made to WO 92/01047, WO 92/20791, WO 93/06213, WO 93/11236, WO 93/19172, WO 95/01438, WO 95/15388, and such.

The amino acid sequence of heavy or light chain variable region may have a substitution, deletion, addition, and/or insertion of one or more amino acids in the amino acid sequence of the heavy or light chain variable region of an antibody whose neutralizing activity against NR10 has been confirmed. Methods well known to those skilled in the art to prepare the amino acid sequence of the heavy or light chain variable region of an antibody having a neutralizing activity against NR10 in which one or more amino acids are substituted, deleted, added, and/or inserted in the amino acid sequence of the heavy or light chain variable region, include methods for introducing mutations into proteins. For example, those skilled in the art can prepare mutants functionally equivalent to the heavy or light chain variable region of the antibody having a neutralizing activity against NR10 by introducing appropriate mutations into the amino acid sequence of the heavy or light chain variable region of the antibody having a neutralizing activity against NR10 using site-directed mutagenesis (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275, Zoller, M J, and Smith, M.(1983) Oligonucleotide-directed mutagenesis of DNA fragments cloned into M13 vectors. Methods Enzymol. 100, 468-500, Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456, Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492) or the like. Thus, the heavy or light chain variable regions of antibodies that contain one or more amino acid mutations in the heavy or light chain variable regions and have a neutralizing activity against NR10 are also included in the heavy or light chain variable regions of the present invention.

When an amino acid residue is altered, the amino acid is preferably mutated for a different amino acid(s) that conserves the properties of the amino acid side-chain. Examples of amino acid side chain properties are: hydrophobic amino acids (A, I, L, M, F, P, W, Y, and V), hydrophilic amino acids (R, D, N, C, E, Q, G, H, K, S, and T), amino acids containing aliphatic side chains (G, A, V, L, I, and P), amino acids containing hydroxyl group-containing side chains (S, T, and Y), amino acids containing sulfur-containing side chains (C and M), amino acids containing carboxylic acid- and amide-containing side chains (D, N, E, and Q), amino acids containing basic side chains (R, K, and H), and amino acids containing aromatic side chains (H, F, Y, and W) (amino acids are represented by one-letter codes in parentheses). Amino acid substitutions within each group are called conservative substitutions. It is already known that a polypeptide containing a modified amino acid sequence in which one or more amino acid residues in a given amino acid sequence are deleted, added, and/or substituted with other amino acids can retain the original biological activity (Mark, D. F. et al., Proc. Natl. Acad. Sci. USA; (1984) 81:5662-6; Zoller, M. J. and Smith, M., Nucleic Acids Res. (1982) 10:6487-500; Wang, A. et al., Science (1984) 224:1431-3; Dalbadie-McFarland, G. et al., Proc. Natl. Acad. Sci. USA (1982) 79:6409-13). Such mutants have an amino acid identity of at least 70%, more preferably at least 75%, even more preferably at least 80%, still more preferably at least 85%, yet more preferably at least 90%, and most preferably at least 95%, with the heavy or light chain variable regions before the amino acid mutations. Herein, sequence identity is defined as the percentage of residues identical to those in the original amino acid sequence of the heavy chain variable region or light chain variable region, determined after the sequences are aligned and gaps are appropriately introduced to maximize the sequence identity as necessary. The identity of amino acid sequences can be determined by the method described above.

Alternatively, the amino acid sequences of heavy or light chain variable regions that have a substitution, deletion, addition, and/or insertion of one or more amino acids in the amino acid sequence of the heavy or light chain variable regions and retain the neutralizing activity against NR10 can be obtained from nucleic acids that hybridize under stringent conditions to nucleic acid composed of the nucleotide sequence encoding the amino acid sequence of the heavy or light chain variable regions. Stringent hybridization conditions to isolate a nucleic acid that hybridizes under stringent conditions to a nucleic acid that includes the nucleotide sequence encoding the amino acid sequence of the heavy or light chain variable regions include, for example, the conditions of 6M urea, 0.4% SDS, 0.5×SSC, and 37° C., or hybridization conditions with stringencies equivalent thereto. With more stringent conditions, for example, the conditions of 6M urea, 0.4% SDS, 0.1×SSC, and 42° C., isolation of nucleic acids with a much higher homology can be expected. The sequences of the isolated nucleic acids can be determined by the known methods described below. The overall nucleotide sequence homology of the isolated nucleic acid is at least 50% or higher sequence identity, preferably 70% or higher, more preferably 90% or higher (for example, 95%, 96%, 97%, 98%, 99%, or higher).

Nucleic acids that hybridize under stringent conditions to a nucleic acid composed of the nucleotide sequence encoding the amino acid sequence of the heavy or light chain variable regions can also be isolated using, instead of the above-described methods using hybridization techniques, gene amplification methods such as polymerase chain reaction (PCR) using primers synthesized based on the information of nucleotide sequence encoding the amino acid sequence of the heavy or light chain variable regions.

Specifically, the identity of one nucleotide sequence or amino acid sequence to another can be determined using the algorithm BLAST, by Karlin and Altschul (Proc. Natl. Acad. Sci. USA (1993) 90, 5873-7). Programs such as BLASTN and BLASTX were developed based on this algorithm (Altschul et al., J. Mol. Biol. (1990) 215, 403-10). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); www.ncbi.nlm.nih.gov).

Alternatively, the antibodies of the present invention may be low-molecular-weight antibodies. The low-molecular-weight antibodies of the present invention include antibody fragments lacking some portions of a whole antibody (for example, whole IgG), and are not particularly limited as long as they retain an NR10-neutralizing activity. The low-molecular-weight antibodies of the present invention are not particularly limited, as long as they contain a portion of whole antibodies. The low-molecular-weight antibodies preferably contain a heavy chain variable region (VH) or light chain variable region (VL). Particularly preferred low-molecular-weight antibodies contain both VH and VL. In addition, preferred examples of the low-molecular-weight antibodies of the present invention include low-molecular-weight antibodies containing CDRs of an antibody. The CDRs contained in the low-molecular-weight antibodies may include some or all of the six CDRs of an antibody.

The low-molecular-weight antibodies of the present invention preferably have a smaller molecular weight than whole antibodies. However, the low-molecular-weight antibodies may form multimers, for example, dimers, trimers, or tetramers, and thus their molecular weights can be greater than those of whole antibodies.

An example of the low-molecular-weight antibodies of the present invention includes scFv antibodies. ScFv antibodies are single-chain polypeptides produced by linking a heavy chain variable region ([VH]) and a light chain variable region ([VL]) via a linker or such (Huston, J. S. et al., Proc. Natl. Acad. Sci. U.S.A. (1988) 85, 5879-5883; Pluckthun "The Pharmacology of Monoclonal Antibodies" Vol. 113, eds., Resenburg and Moore, Springer Verlag, New York, pp. 269-315, (1994)). The order of the heavy chain and light chain variable regions to be linked together is not particularly limited, and they may be arranged in any order. Examples of the arrangement are listed below.

[VH] linker [VL]
[VL] linker [VH]

The amino acid sequence of the heavy chain variable region or light chain variable region may contain a substitution, deletion, addition, and/or insertion. Furthermore, the heavy chain variable region and light chain variable region may also lack some portions or be added with other polypeptides, as long as they have antigen binding activity when linked together. Alternatively, the variable regions may be chimerized or humanized.

In the present invention, linkers which bind the variable regions of the antibody include arbitrary peptide linkers that can be introduced using genetic engineering, or synthetic linkers such as those disclosed in Protein Engineering, 9(3), 299-305, 1996.

The preferred linkers in the present invention are peptide linkers. The lengths of the peptide linkers are not particularly limited and those skilled in the art can appropriately select the lengths depending on the purpose. Typical lengths are one to 100 amino acids, preferably 3 to 50 amino acids, more preferably 5 to 30 amino acids, and particularly preferably 12 to 18 amino acids (for example, 15 amino acids).

Amino acid sequences of such peptide linkers include, for example:

Ser;

Gly-Ser;

Gly-Gly-Ser;

Ser-Gly-Gly;

| Gly-Gly-Gly-Ser; | (SEQ ID NO: 8) |
| Ser-Gly-Gly-Gly; | (SEQ ID NO: 9) |
| Gly-Gly-Gly-Gly-Ser; | (SEQ ID NO: 10) |
| Ser-Gly-Gly-Gly-Gly; | (SEQ ID NO: 11) |
| Gly-Gly-Gly-Gly-Gly-Ser; | (SEQ ID NO: 12) |
| Ser-Gly-Gly-Gly-Gly-Gly; | (SEQ ID NO: 13) |
| Gly-Gly-Gly-Gly-Gly-Gly-Ser; | (SEQ ID NO: 14) |
| Ser-Gly-Gly-Gly-Gly-Gly-Gly; | (SEQ ID NO: 15) |

(Gly-Gly-Gly-Gly-Ser (SEQ ID NO: 10))n;
and (Ser-Gly-Gly-Gly-Gly (SEQ ID NO: 11))n, where n is an integer of 1 or larger.

Synthetic chemical linkers (chemical crosslinking agents) include crosslinking agents that are routinely used to crosslink peptides, for example, N-hydroxy succinimide (NHS), disuccinimidyl suberate (DSS), bis(sulfosuccinimidyl) suberate ($BS^3$), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), and bis[2-(sulfosuccinimidoxycarbonyloxy)ethyl]sulfone (sulfo-BSOCOES). These crosslinking agents are commercially available.

The antibodies of the present invention include antibodies in which two or more amino acid residues have been added to the amino acid sequence of an antibody of the present invention. Further, fusion proteins which result from a fusion between one of the above antibodies and a second peptide or protein is included in the present invention. The fusion proteins can be prepared by ligating a polynucleotide encoding an antibody of the present invention and a polynucleotide encoding a second peptide or polypeptide in frame, inserting this into an expression vector, and expressing the fusion construct in a host. Some techniques known to those skilled in the art are available for this purpose. The partner peptide or polypeptide to be fused with an antibody of the present invention may be a known peptide, for example, FLAG (Hopp, T. P. et al., BioTechnology 6, 1204-1210 (1988)), 6×His consisting of six His (histidine) residues, 10×His, influenza hemagglutinin (HA), human c-myc fragment, VSV-GP fragment, p18HIV fragment, T7-tag, HSV-tag, E-tag, SV40 T antigen fragment, lck tag, α-tubulin fragment, B-tag, and Protein C fragment. Other partner polypeptides to be fused with the antibodies of the present invention include, for example, GST (glutathione-S-transferase), HA (influenza hemagglutinin), immunoglobulin constant region, β-galactosidase, and MBP (maltose-binding protein). A polynucleotide encoding one of these commercially available peptides or polypeptides can be fused with a polynucleotide encoding an antibody of the present invention. The fusion polypeptide can be prepared by expressing the fusion construct.

Furthermore, the antibodies of the present invention may be conjugated antibodies which are linked to any of various molecules including polyethylene glycol (PEG), hyaluronic acid, radioactive substances, fluorescent substances, luminescent substances, enzymes, and toxins. Such conjugated antibodies can be obtained by chemically modifying the obtained antibodies. Methods for modifying antibodies have been established in this field (for example, U.S. Pat. No. 5,057,313 and U.S. Pat. No. 5,156,840). The "antibodies" of the present invention also include such conjugated antibodies.

In addition, a preferred embodiment of the anti-NR10 antibodies in the present invention includes, without particular limitation, antibodies that recognize domain 1. In the present invention, domain 1 refers to the region of amino acids at positions 21 to 120 (LPAKP to LENIA) in the amino acid sequence of human NR10 of SEQ ID NO: 7, where the amino acid numbering is based on the sequence including the signal peptide.

The antibodies of the present invention may differ in amino acid sequence, molecular weight, isoelectric point, presence/absence of sugar chains, and conformation depending on the cell or host producing the antibody or the purification method as described below. However, a resulting antibody is included in the present invention as long as it has a function as an NR10 antagonist. For example, when an antibody of the present invention is expressed in prokaryotic cells, for example $E. coli$, a methionine residue is added to the N terminus of the original antibody amino acid sequence. Such antibodies are included in the present invention.

Monoclonal antibodies having a neutralizing activity against NR10 can be obtained, for example, by the following procedure: anti-NR10 monoclonal antibodies are prepared by using as an antigen NR10 or a fragment thereof that is derived from a mammal such as human or mouse by known methods, and then antibodies having a neutralizing activity against NR10 are selected from the thus obtained anti-NR10 monoclonal antibodies. Specifically, a desired antigen or cells expressing the desired antigen are used as a sensitizing antigen for immunization according to conventional immunization methods. Anti-NR10 monoclonal antibodies can be prepared by fusing the obtained immune cells with known parental cells using conventional cell fusion methods, and screening them for monoclonal antibody-producing cells (hybridomas) by conventional screening methods. Animals to be immunized include, for example, mammals such as mice, rats, rabbits, sheep, monkeys, goats, donkeys, cows, horses, and pigs. The antigen can be prepared using the known NR10 gene sequence according to known methods, for example, by methods using baculovirus (for example, WO 98/46777).

Hybridomas can be prepared, for example, according to the method of Milstein et al. (Kohler, G. and Milstein, C., Methods Enzymol. (1981) 73: 3-46) or such. When the immunogenicity of an antigen is low, immunization may be performed after linking the antigen with a macromolecule having immunogenicity, such as albumin.

Embodiments of the antibodies of the present invention that have a neutralizing activity against NR10 include monoclonal antibodies that have a neutralizing activity against human NR10. Antigens used to prepare monoclonal antibodies that have a neutralizing activity against human NR10 are not particularly limited, as long as they enable preparation of antibodies that have a neutralizing activity against human NR10. For example, it is known that there are a number of variants of human NR10, and any variant may be used as an immunogen as long as it enables preparation of antibodies that have a neutralizing activity against human NR10. Alternatively, under the same condition, a peptide fragment of NR10 or a protein in which artificial mutations have been introduced into the natural NR10 sequence may be used as an immunogen. Human NR10.3 is one of preferred immunogens in preparing antibodies that have an activity of binding and/or neutralizing NR10 in the present invention.

Furthermore, the neutralizing activity of antibody against NR10 can be measured, for example, by observing the effect of suppressing the growth of the IL-31-dependent cell line as described in the Referential Examples.

Meanwhile, monoclonal antibodies can also be obtained by DNA immunization. DNA immunization is a method in which a vector DNA constructed such that the gene encoding an antigen protein can be expressed in an animal to be immunized is administered to the animal, and the immunogen is expressed within the body of the animal to provide immunostimulation. As compared to common immunization methods based on the administration of protein antigens, the DNA immunization is expected to be advantageous in that:

it enables immunostimulation while retaining the structure of a membrane protein; and the immunogen does not need to be purified.

On the other hand, it is difficult to combine DNA immunization with an immunostimulating means such as an adjuvant.

In order to obtain a monoclonal antibody by DNA immunization, first, DNA encoding NR10 is administered to an animal to be immunized. The DNA encoding NR10 can be synthesized by known methods such as PCR. The resulting DNA is inserted into an appropriate expression vector, and administered to the animal to be immunized. Expression vectors that can be used include commercially available expression vectors such as pcDNA3.1. The vector can be administered to the living body by conventional methods. For example, DNA immunization can be carried out by introducing gold particles coated with the expression vector into cells by gene gun. Booster using NR10-expressing cells after DNA immunization is a preferred method to yield a monoclonal antibody.

Once the mammal is immunized as described above and the serum level of a desired antibody is confirmed to be increased, immune cells are collected from the mammal and subjected to cell fusion. Preferred immune cells are spleen cells in particular.

Mammalian myeloma cells are used for fusion with the above immune cells. It is preferred that myeloma cells have appropriate selection markers for screening. The selection marker refers to a phenotype that allows (or does not allow) survival under particular culture conditions. Known selection markers include hypoxanthine-guanine phosphoribosyltransferase deficiency (hereinafter abbreviated as "HGPRT deficiency") and thymidine kinase deficiency (hereinafter abbreviated as "TK deficiency"). HGPRT- or TK-deficient cells exhibit hypoxanthine-aminopterin-thymidine sensitivity (hereinafter abbreviated as "HAT sensitivity"). In HAT selection medium, HAT-sensitive cells cannot synthesize DNA and thus will die. However, when fused with normal cells, they can continue to synthesize DNA via the salvage pathway of the normal cells and thus can grow even in HAT selection medium.

HGPRT- or TK-deficient cells can be selected using a medium containing 6-thioguanine, 8-azaguanine (hereinafter abbreviated as "8AG"), or 5'-bromodeoxyuridine. While normal cells are killed due to incorporation of these pyrimidine analogs into DNA, cells lacking these enzymes can survive in the selection medium because they cannot incorporate these pyrimidine analogs. Another selection marker called G418 resistance confers resistance to 2-deoxystreptamine antibiotics (gentamicin analogs) due to the neomycin resistance gene. Various myeloma cells suitable for cell fusion are known.

Cell fusion between immune cells and myeloma cells can be essentially carried out according to known methods, for example, the method by Kohler and Milstein (Kohler. G. and Milstein, C., Methods Enzymol. (1981) 73, 3-46).

More specifically, cell fusion can be carried out, for example, in a common culture medium in the presence of a cell fusion-promoting agent. The fusion-promoting agent includes, for example, polyethylene glycol (PEG) and Sendai virus (HVJ). If required, an auxiliary agent such as dimethyl sulfoxide may also be added to improve fusion efficiency.

The immune cells and myeloma cells may be used at an arbitrarily determined ratio. For example, the ratio of immune cells to myeloma cells is preferably from 1 to 10. Culture media to be used for cell fusion include, for example, media that are suitable for the cell growth of myeloma cell line, such as RPMI 1640 and MEM, and other common culture media used for this type of cell culture. In addition, the culture media may also be supplemented with serum supplement such as fetal calf serum (FCS).

Predetermined amounts of immune cells and myeloma cells are mixed well in the culture medium, and then mixed with a PEG solution pre-heated to 37° C. to produce fused cells (hybridomas). In the cell fusion method, for example, PEG with mean molecular weight of about 1,000-6,000 can be added to the cells typically at a concentration of 30% to 60% (w/v). Then, successive addition of the appropriate culture medium listed above and removal of supernatant by centrifugation are repeated to eliminate the cell fusion agent and such, which are unfavorable to the growth of hybridomas.

The resulting hybridomas can be screened using a selection medium according to the selection marker possessed by myeloma cells used in the cell fusion. For example, HGPRT- or TK-deficient cells can be screened by culturing them in a HAT medium (a medium containing hypoxanthine, aminopterin, and thymidine). Specifically, when HAT-sensitive myeloma cells are used in cell fusion, cells successfully fused with normal cells can be selectively grown in the HAT medium. The cell culture using the above HAT medium is continued for a sufficient period of time to allow all cells except the desired hybridomas (non-fused cells) to die. Specifically, in general, the desired hybridomas can be selected by culturing the cells for several days to several weeks. Then, screening and single cloning of hybridomas that produce an antibody of interest can be carried out by performing ordinary limiting dilution methods. Alternatively, antibodies that recognize NR10 can be prepared by the method described in WO 03/104453.

Screening and single cloning of an antibody of interest can be suitably carried out by known screening methods based on antigen-antibody reaction. For example, an antigen is bound to a carrier such as beads made of polystyrene or such and commercially available 96-well microtiter plates, and then reacted with the culture supernatant of hybridoma. Next, the carrier is washed and then reacted with an enzyme-labeled secondary antibody or such. When the culture supernatant contains an antibody of interest reactive to the sensitizing antigen, the secondary antibody binds to the carrier via this antibody. Finally, the secondary antibody bound to the carrier is detected to determine whether the culture supernatant contains the antibody of interest. Hybridomas producing a desired antibody capable of binding to the antigen can be cloned by the limiting dilution method or such. Not only the antigen used for immunization but also an NR10 protein substantially equivalent thereto can be preferably used as an antigen for this purpose. For example, a cell line expressing NR10, the extracellular domain of NR10, or an oligopeptide composed of a partial amino acid sequence constituting the domain may be used as the antigen.

In addition to the above-described method for preparing hybridomas through immunization of a nonhuman animal with an antigen, antibodies of interest can also be obtained by sensitizing human lymphocytes with an antigen. Specifically, first, human lymphocytes are sensitized with an NR10 protein in vitro. Then, the sensitized lymphocytes are fused with an appropriate fusion partner. For example, human-derived myeloma cells with the ability to divide permanently can be used as the fusion partner (see Japanese Patent Application Kokoku Publication No. (JP-B) H1-59878 (examined, approved Japanese patent application published for opposition)). Antibodies obtained by this method are human antibodies having an activity of binding to the NR10 protein.

The antibodies obtained by the above-described method can be produced by methods known to those skilled in the art. For example, based on the sequence of the NR10-recognizing antibody, the antibody can be produced by genetic recombination techniques known to those skilled in the art. Specifically, a polynucleotide encoding an antibody can be constructed based on the sequence of the NR10-recognizing antibody, inserted into an expression vector, and then expressed in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

The vectors include M13 vectors, pUC vectors, pBR322, pBluescript, and pCR-Script. Alternatively, when aiming to subclone and excise cDNA, the vectors include, for example, pGEM-T, pDIRECT, and pT7, in addition to the vectors described above. Expression vectors are particularly useful when using vectors for producing the antibodies of the present invention. For example, when aiming for expression in E. coli such as JM109, DH5α, HB101, and XL1-Blue, the expression vectors not only have the above-described characteristics that allow vector amplification in E. coli, but must also carry a promoter that allows efficient expression in E. coli, for example, lacZ promoter (Ward et al., Nature (1989) 341, 544-546; FASEB J. (1992) 6, 2422-2427), araB promoter (Better et al., Science (1988) 240, 1041-1043), T7 promoter or such. Such vectors include pGEX-5X-1 (Pharmacia), "QIAexpress system" (Qiagen), pEGFP, or pET (in this case, the host is preferably BL21 that expresses T7 RNA polymerase) in addition to the vectors described above.

The vectors may contain signal sequences for antibody secretion. As a signal sequence for antibody secretion, a pelB signal sequence (Lei, S. P. et at J. Bacteriol. (1987) 169, 4379) may be used when a protein is secreted into the E. coli periplasm. The vector can be introduced into host cells by calcium chloride or electroporation methods, for example.

In addition to vectors for *E. coli*, the vectors for producing the antibodies of the present invention include mammalian expression vectors (for example, pcDNA3 (Invitrogen), pEF-BOS (Nucleic Acids. Res. 1990, 18(17), p5322), pEF, and pCDM8), insect cell-derived expression vectors (for example, the "Bac-to-BAC baculovirus expression system" (Gibco-BRL) and pBacPAK8), plant-derived expression vectors (for example, pMH1 and pMH2), animal virus-derived expression vectors (for example, pHSV, pMV, and pAdex-Lcw), retroviral expression vectors (for example, pZIPneo), yeast expression vectors (for example, "*Pichia* Expression Kit" (Invitrogen), pNV11, and SP-Q01), and *Bacillus subtilis* expression vectors (for example, pPL608 and pKTH50), for example.

When aiming for expression in animal cells such as CHO, COS, and NIH3T3 cells, the vectors must have a promoter essential for expression in cells, for example, SV40 promoter (Mulligan et al., Nature (1979) 277, 108), MMLV-LTR promoter, EF1α promoter (Mizushima et al., Nucleic Acids Res. (1990) 18, 5322), and CMV promoter, and more preferably they have a gene for selecting transformed cells (for example, a drug resistance gene that allows evaluation using an agent (neomycin, G418, or such). Vectors with such characteristics include pMAM, pDR2, pBK-RSV, pBK-CMV, pOPRSV, and pOP13, for example.

In addition, the following method can be used for stable gene expression and gene amplification in cells: CHO cells deficient in a nucleic acid synthesis pathway are introduced with a vector (for example, pSV2-dhfr (Molecular Cloning $2^{nd}$ edition, Cold Spring Harbor Laboratory Press, 1989)) that carries a DHFR gene which compensates for the deficiency, and the vector is amplified using methotrexate (MTX). Alternatively, the following method can be used for transient gene expression: COS cells with a gene expressing SV40 T antigen on their chromosome are transformed with a vector (pcD and such) with an SV40 replication origin. Replication origins derived from polyoma virus, adenovirus, bovine papilloma virus (BPV), and such can also be used. To amplify gene copy number in host cells, the expression vectors may further carry selection markers such as aminoglycoside transferase (APH) gene, thymidine kinase (TK) gene, *E. coli* xanthine-guanine phosphoribosyltransferase (Ecogpt) gene, and dihydrofolate reductase (dhfr) gene.

The antibodies of the present invention obtained by the methods described above can be isolated from inside host cells or from outside the cells (the medium, or such), and purified to homogeneity. The antibodies can be isolated and purified by methods routinely used for isolating and purifying antibodies, and the type of method is not limited. For example, the antibodies can be isolated and purified by appropriately selecting and combining column chromatography, filtration, ultrafiltration, salting out, solvent precipitation, solvent extraction, distillation, immunoprecipitation, SDS-polyacrylamide gel electrophoresis, isoelectrofocusing, dialysis, recrystallization, and such.

The chromatographies include, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). The chromatographic methods described above can be conducted using liquid chromatography, for example, HPLC and FPLC. Columns that can be used for affinity chromatography include protein A columns and protein G columns. Columns using protein A include, for example, Hyper D, POROS, and Sepharose FF (GE Amersham Biosciences). The present invention includes antibodies that are highly purified using these purification methods.

The NR10-binding activity of the antibodies can be determined by methods known to those skilled in the art. Methods for determining the antigen-binding activity of an antibody include, for example, ELISA (enzyme-linked immunosorbent assay), EIA (enzyme immunoassay), RIA (radioimmunoassay), and fluorescent antibody method. For example, when enzyme immunoassay is used, antibody-containing samples, such as purified antibodies and culture supernatants of antibody-producing cells, are added to antigen-coated plates. A secondary antibody labeled with an enzyme, such as alkaline phosphatase, is added and the plates are incubated. After washing, an enzyme substrate, such as p-nitrophenyl phosphate, is added, and the absorbance is measured to evaluate the antigen-binding activity.

Moreover, the neutralizing activity of an antibody against NR10 can be determined, for example, by the method described in the Reference Examples, in which the growth inhibition effect on the IL-31-depenedent cell line is observed.

The NR10 antagonists or antibodies having a neutralizing activity against NR10 in the present invention can be used as preventive or therapeutic agents for pruritus. The present inventors administered antibodies having a neutralizing activity against mouse NR10 to pruritus model animals and demonstrated that the antibodies produced a marked therapeutic effect. Furthermore, non-antibody NR10 antagonists are also expected to have a therapeutic effect against pruritus as observed in the Examples.

The present inventors discovered that antagonistic antibodies against NR10 had a therapeutic effect on pruritus. On the other hand, it was revealed that in the acute contact dermatitis model and the DSS acute colitis model, anti-NR10 antagonistic antibodies had no therapeutic effect against these diseases themselves.

In the present invention, the treatment of pruritus is distinguished from the treatment of diseases and symptoms that cause pruritus (for example, the diseases described below, such as atopic dermatitis and type C hepatitis). Therefore, the therapeutic or preventive agents of the present invention for pruritus target pruritus itself, and they are not for treating or preventing diseases and symptoms that cause pruritus. The therapeutic or preventive agents of the present invention are administered to patients in need of treatment or prevention of pruritus for the purpose of treating or preventing pruritus, but not for the purpose of treating or preventing diseases and symptoms that cause pruritus.

Pruritus to be treated by the present invention is not particularly limited, and may be any type of pruritus. Specific examples of pruritus to be treated by the present invention include, for example, pruritus in scabies, pediculation, bug bites and stings, urticaria, atopic dermatitis, contact dermatitis, lichen planus, miliaria, dermatitis herpetiformis, xeroderma, biliary obstruction, primary biliary cirrhosis (PBC), infectious hepatitis such as type C hepatitis, uremia, chronic renal failure, renal dialysis, lymphoma, leukemia, polycythemia rubra vera, pregnancy, ingestion of drugs (barbiturate, salicylate, etc.), hyperthyroidism, diabetes mellitus, and organ cancers.

The preventive or therapeutic agents of the present invention for pruritus comprise as an active ingredient the above-described NR10 antagonist or antibody having a neutralizing activity against NR10. The phrase "comprise an NR10 antagonist as an active ingredient" means containing an NR10 antagonist as at least one active ingredient, and does not limit the content of the NR10 antagonist. The therapeutic or preventive agents of the present invention for pruritus may contain other ingredients that promote the prevention or treatment of pruritus, in combination with the NR10 antagonist.

Pruritus for which the therapeutic or preventive agents of the present invention are used is not particularly limited, and may be developed by any cause; however, preferred pruritus is pruritus involving IL-31. Such pruritus involving IL-31 includes pruritus caused by IL-31 and pruritus with high expression of IL-31.

The NR10 antagonists of the present invention may be prepared as formulations according to standard methods (see, for example, Remington's Pharmaceutical Science, latest edition, Mark Publishing Company, Easton, USA). Further, they may contain pharmaceutically acceptable carriers and/or additives if necessary. For example, they may contain surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, without limitation to these, the agents for preventing or treating inflammatory diseases of the present invention may contain other commonly used carriers. Such carriers specifically include light anhydrous silicic acid, lactose, crystalline cellulose, mannitol, starch, carmelose calcium, carmelose sodium, hydroxypropylcellulose, hydroxypropylmethylcellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, and inorganic salt. The agents may also contain other low-molecular-weight polypeptides, proteins such as serum albumin, gelatin, and immunoglobulin, and amino acids such as glycine, glutamine, asparagine, arginine, and lysine. When the NR10 antagonist is prepared as an aqueous solution for injection, the NR10 antagonist may be dissolved in an isotonic solution containing, for example, physiological saline, dextrose, or other adjuvants. The adjuvants may include, for example, D-sorbitol, D-mannose, D-mannitol, and sodium chloride. In addition, appropriate solubilizing agents, for example, alcohols (for example, ethanol), polyalcohols (for example, propylene glycols and PEGs), and non-ionic detergents (polysorbate 80 and HCO-50) may be used concomitantly.

If necessary, NR10 antagonists may be encapsulated in microcapsules (microcapsules made of hydroxymethylcellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition" &, Oslo Ed. (1980)). Moreover, methods for making sustained-release drugs are known, and these can be applied for NR10 antagonists (Langer et al., J. Biomed. Mater. Res. (1981) 15, 167-277; Langer, Chem. Tech. (1982) 12, 98-105; U.S. Pat. No. 3,773, 919; European Patent Application (EP) No. 58,481; Sidman et al., Biopolymers (1983) 22, 547-56; EP 133,988).

The agents for preventing or treating pruritus of the present invention can be administered either orally or parenterally, but are preferably administered parenterally. Specifically, the agents are administered to patients by injection or percutaneous administration. Injections include, for example, intravenous injections, intramuscular injections, and subcutaneous injections, for systemic or local administration. The agents may be given to sites where inflammation is to be suppressed, or areas surrounding the sites by local infusion, intramuscular injection in particular. The administration methods can be properly selected according to the patient's age and condition. The single-administration dose can be selected, for example, from within the range of 0.0001 to 100 mg of the active ingredient per kg body weight. Alternatively, for example, when the agents are administered to human patients, the dose of the active ingredient can be selected from within the range of 0.001 to 1,000 mg/kg body weight. The single-administration dose preferably contains, for example, about 0.01 to 50 mg/kg body weight of an NR10 antagonist. However, the dose of an agent for preventing or treating pruritus of the present invention is not limited to these examples.

The present invention also provides therapeutic agents for pruritus, which comprise an IL-31 antagonist as an active ingredient. Such IL-31 antagonists are not particularly limited, as long as they are substances that inhibit the biological activity of IL-31 by binding to IL-31. Preferred IL-31 antagonists include, for example, anti-IL-31 antibodies (for example, WO 2006/088955, WO 2006/88956, and WO 2006/122079). Preparation, alteration, modification, production, purification, administration, formulation, and such of anti-IL-31 antibodies can be performed according to the above description regarding the anti-NR10 antibodies.

All prior art documents cited in the present specification are incorporated herein by reference.

EXAMPLES

Hereinbelow, the present invention is specifically described using Examples, but it is not to be construed as being limited thereto.

Example 1

Assessment of IL-31-Induced Scratching Behavior

Ten µg of mouse IL-31 (in house) was intravenously administered to 9-week-old normal female BALB/c mice (Charles River Laboratories Japan). The scratching behavior was monitored and analyzed for 12 hours immediately after administration using a scratching counting system (Micro-Act; NeuroScience Inc.). As a result, the IL-31-administered group (n=8) showed a significant increase in the number of scratchings with a peak at about five hours after the administration, as compared to the group administered with a vehicle (PBS containing 0.5% BALB/c mouse serum) (n=8). This IL-31-induced scratching behavior was completely suppressed by intravenous administration of 350 mg/kg BM095, an anti-mouse NR10 neutralizing antibody, prior to IL-31 administration (n=8) (FIG. 1). This result demonstrates that the anti-NR10 neutralizing antibody has an effect of suppressing IL-31-induced pruritus.

Effect of Anti-NR10 Neutralizing Antibody in Mite Antigen-Induced Dermatitis Model Five µg of *Dermatophagoides pteronyssinus* (Dp) crude extract (Cosmo Bio LSL) was administered as a mite antigen intradermally to 9-week-old SPF female NC/Nga Tnd Crlj mice (Charles River Laboratories Japan) on the ventral side of their ears three times a week for three weeks to induce dermatitis (Int Arch Allergy Immunol 2004; 133:55-63). In the solvent control group for Dp, 5 µl of normal saline (Otsuka Pharmaceutical Co.) was administered on the same schedule (n=7). In this pathological model, the anti-mouse NR10 neutralizing antibody BM-095 was intravenously administered at 20 mg/kg on days 0, 3, 7, 10, 14, 17, and 21 (n=8). For a vehicle control group, 200 mmol/L NaCl/20 mmol/L sodium acetate buffer (pH 5.5) was intravenously administered on the same schedule (n=8).

Figure 2:
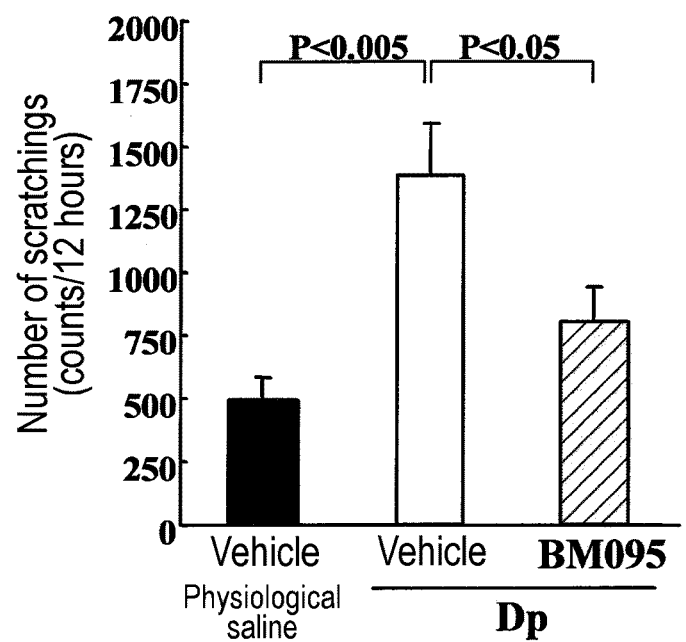
FIG. 2 is a graph showing the assessment of mite antigen-induced scratching behavior. Mean±standard error.

The pruritus was assessed by counting the number of scratchings during the measuring time of 12 hours on day 21 using a scratching counting system (MicroAct; NeuroScience Inc.). The result showed that the number of scratchings was significantly increased in the vehicle control group as compared to the solvent control group for Dp (p<0.005). In the BM095-administered group, the number of scratchings was significantly reduced as compared to the vehicle control group (p<0.05) (FIG. 2).

This result demonstrates that the anti-NR10 neutralizing antibody has a suppressing effect against pruritus.

Example 2

Suppressing Effect of H0L0 Against IL-31-Induced Pruritus in Cynomolgus Monkeys

Figure 5:
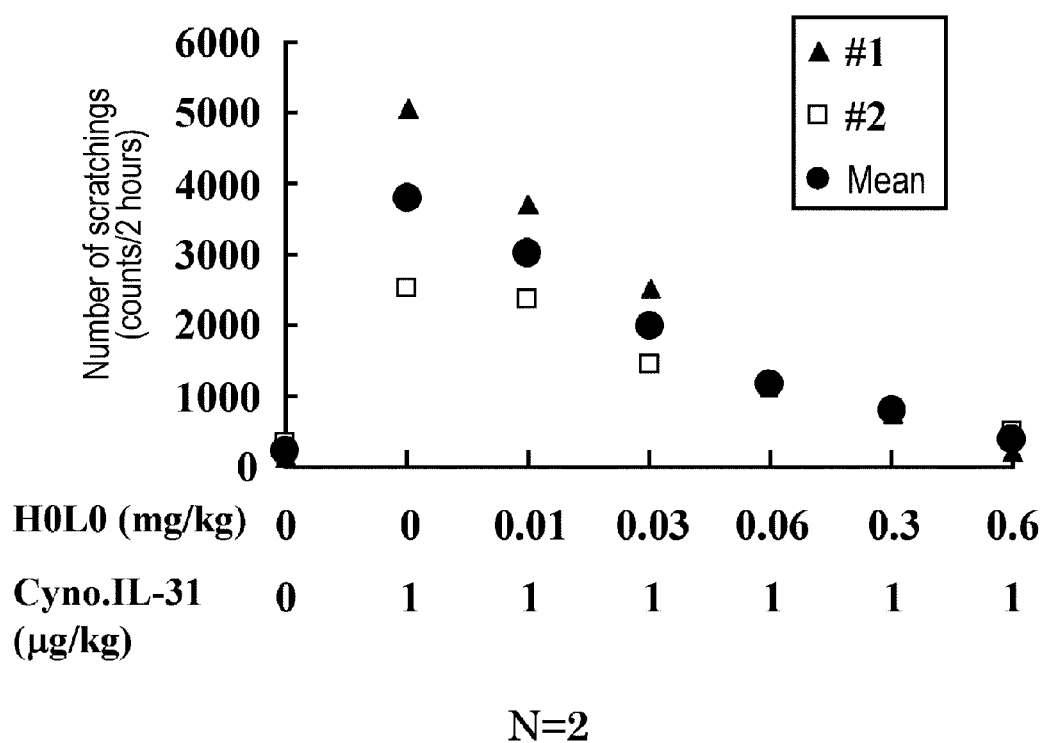
FIG. 5 is a graph showing the pruritus-suppressing effect of anti-NR10 antibody H0L0 assessed using the number of scratchings as an indicator.

The effect of anti-human NR10 antibody H0L0 (heavy chain amino acid sequence/SEQ ID NO: 17; light chain amino acid sequence/SEQ ID NO: 18) on pruritus induced by intravenously administering cynomolgus IL-31 to 4- to 5-year-old cynomolgus monkeys was examined. PBS (vehicle) or H0L0 was intravenously administered at 0.01, 0.03, 0.06, 0.3, and 0.6 mg/kg. Twenty-four hours after intravenous administration, 1 g/kg of cynomolgus IL-31 was intravenously administered, and then the behavior was recorded with a video camera for two hours. The number of scratchings was counted while replaying the recorded video, assuming three or more consecutive scratching actions as a scratching. The result showed that H0L0 reduced the number of cynomolgus IL-31-induced scratchings in a dose-dependent manner (FIG. 5). This result demonstrates that the anti-NR10 antibody H0L0 has a suppressing effect against pruritus.

Referential Example 1

Establishment of NR10- and OSMR-Expressing Ba/F3 Cell Lines

The human NR10 cDNA (WO 00/75314 SEQ ID NO: 1/SEQ ID NO: 16) was inserted into the expression vector pCOS1 (Biochem. Biophys. Res. Commun. 228, p838-45, 1996), and the resulting vector was named pCosNR10.3. An oncostatin M receptor cDNA (OSMR, GenBank accession No. NM003999) was isolated by PCR from a human placental library, and the expression vector pCos1-hOSMR was constructed in the same manner. 10 μg each of the vectors were simultaneously introduced into mouse IL-3-dependent pro-B cell-derived cell line Ba/F3 by electroporation (BioRad Gene Pulser, 960 μF, 0.33 kV). After introduction, human IL-31 was added, and the cells were cultured to obtain a cell line that proliferates in an IL-31-dependent manner. In the same manner, a mouse IL-31-dependent cell line was also produced from Ba/F3 cells expressing the mouse NR10 and mouse OSMR genes.

Both cell lines exhibited an ED50 of several ng/ml and well proliferated. The human IL-31-dependent cell line did not respond to mouse IL-31, and was suppressed by addition of human NR10 protein (extracellular domain). Meanwhile, the mouse IL-31-dependent cell line did not respond to human IL-31, and was not suppressed by addition of mouse NR10 protein (extracellular domain).

Referential Example 2

Preparation of NR10 Protein (Extracellular Domain)

The human NR10 cDNA was used as a template to amplify only the extracellular domain by PCR. The amplified region was then attached to a FLAG tag sequence at the C terminus and inserted to the expression vector pCXND3 (WO2005/005636) (pCXND3-NR10-flag). Ten μg of the linearized vector was introduced into Chinese hamster ovary cell line DG44 by electroporation (BioRad Gene PulserII, 25 μF, 1.5 kV). A cell line showing high level expression was obtained. The supernatant of the cell line cultured on a large scale was purified using anti-FLAG antibody column (Sigma) and gel filtration to obtain a purified sample, which was subjected to the experiments described below. Mouse NR10 (extracellular domain) in which a FLAG tag sequence has been added at the C terminus was also produced in the same manner.

Referential Example 3

Isolation of scFv Having Anti-Mouse NR10-Neutralizing Activity and Preparation of Chimeric IgG BM095

Candidate clones were screened from a human antibody phage library by the panning method using biotinylated mouse NR10 protein (extracellular domain). Secretory scFvs were purified from these clones and added to the IL-31-dependent Ba/F3 cell growth assay system described in Referential Example 1. As a result, a clone exhibiting a strong growth-suppressing activity, BM095, was successfully obtained.

The sequences of human H chain variable region (VH) and light chain variable region (VL) of BM095 were linked to mouse IgG2a constant region (after CH1) and λ chain constant region, respectively, by PCR to construct an expression vector. This VH amino acid sequence is shown in SEQ ID NO: 1, and the nucleotide sequence encoding the amino acid sequence is shown in SEQ ID NO: 2. The VL amino acid sequence is shown in SEQ ID NO: 3, and the nucleotide sequence encoding the amino acid sequence is shown in SEQ ID NO: 4. The respective linearized expression vectors were simultaneously introduced into DG44 cells, and a cell line expressing the chimeric IgG at a high level was selected. A purified sample was obtained from the supernatant of a large-scale culture of this cell line by Protein A (rProtein A Sepharose Fast Flow, GE Amersham Biosciences) column chromatography and cation exchange (SP-TOYOPEARL 650M, TOSOH) column chromatography. Then, ActiClean Etox (Sterogen) resin was used to reduce pyrogens below the detection limit.

Referential Example 4

Efficacy of BM095 on Dextran Sulfate Sodium (DSS)-Induced Colitis

The DSS-induced colitis model (J Immunol 2003; 171: 5507-5513), which has been reported as a pathological model for inflammatory bowel disease (IBD), was prepared to examine the effect of BM-095, an anti-mouse NR10 neutralizing antibody. An aqueous solution of 5% (w/v) dextran sulfate sodium salt (Wako Pure Chemical Industries) was prepared using distilled water sterilized by filtration with 0.22-μm filter (Millipore). Six-week-old male Balb/cAnN Crj mice (Charles River Laboratories Japan) were allowed to freely consume the solution from water bottles for seven days. The body weights were measured, and the percent change in the body weight relative to that on the first day of DSS administration was used to assess the drug efficacy.

In order to test whether the pathological condition is improved in this model by neutralization of IL-31 signaling, the anti-mouse NR10 neutralizing antibody BM095 was intravenously administered at 10 mg/kg on the day before DSS administration, and the weight loss was assessed (n=10). To the vehicle control group, the vehicle (a mixture of acetate buffer (20 mmol/L sodium acetate, 20 mmol/L sodium chloride) and phosphate-buffered saline (PBS; GIBCO) at a volume ratio of 1:5) was intravenously administered on the day before DSS administration (vehicle group; n=10). Furthermore, percent body weight changes of a Balb/cAnN Crj mouse of the same age and sex as those in the DSS administration group were also monitored (n=1) to evaluate percent body weight changes of normal mouse.

Figure 3:
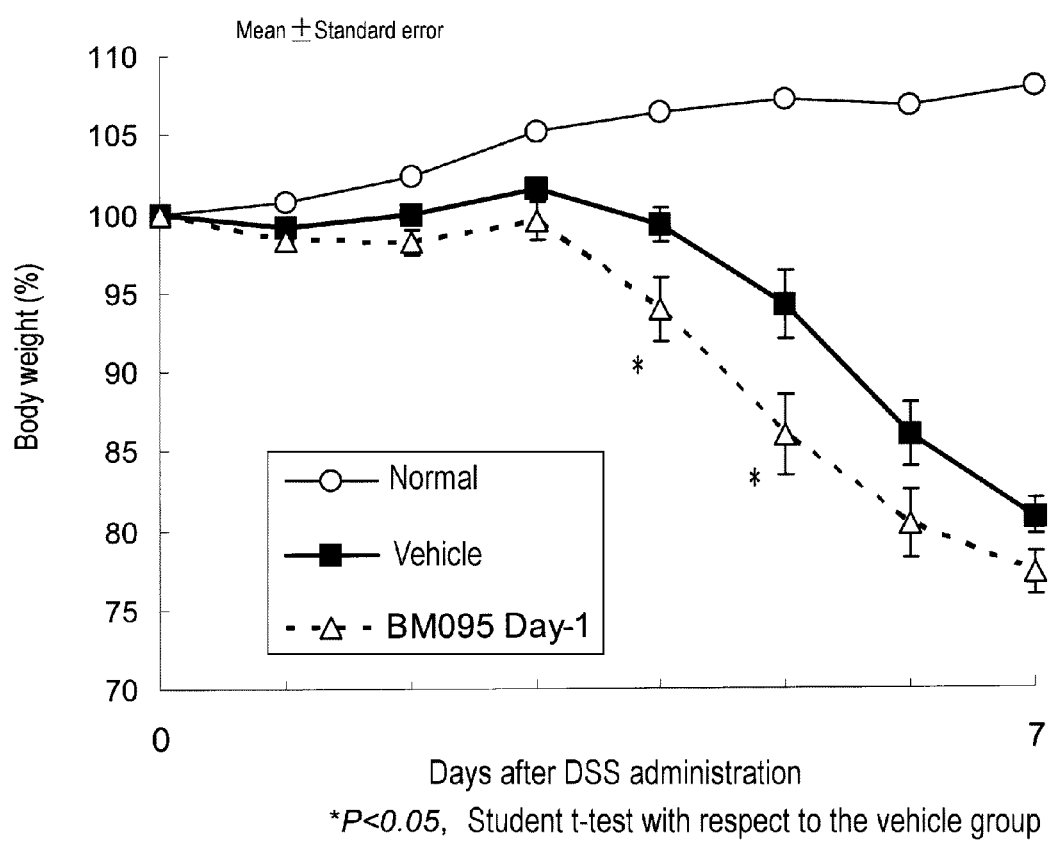
FIG. 3 is a graph showing the time course of percent body weight changes in DSS colitis model mice.

The time course of body weight changes is shown in FIG. 3. DSS administration resulted in a decrease in the percent body weight in the vehicle group. On the other hand, the BM095-administered group showed similar body weight changes to the vehicle group; however, after four and five days of the DSS administration, a significant decrease of the percent body weight was observed in the BM095 group as compared to the vehicle group. From these results, BM095 administration had no therapeutic effect on colitis in this model.

Although IL-31RA expression was reported to be enhanced in this model (WO 2004/003140), the above experimental results revealed that neutralizing antibodies against the molecule had no therapeutic effect against colitis in this model.

Referential Example 5

Efficacy of BM095 on Picryl Chloride-Induced Acute Contact Dermatitis Model

Dermatitis resulting from delayed hypersensitivity reaction sensitized/induced by picryl chloride application, which has been reported as an acute contact dermatitis model (Clin Immunol 2003; 108: 257-262), was created to assess the effect of BM-095, an anti-mouse NR10 neutralizing antibody. Eight-week-old female Balb/cAnN Crj mice (Charles River Laboratories Japan) were sensitized by applying 50 µL of 7% picryl chloride (nacalai tesque, Inc.) solution (ethanol: acetone=3:1, v/v) onto the abdominal skin. After five days, contact dermatitis was elicited by applying 20 µL of 1% picryl chloride solution (acetone: olive=1:4, v/v) onto the skin of right auricle (induction). For a control for assessing the influence of the solvent on the auricular thickness, 20 µl of the solvent (acetone: olive=1:4, v/v) was applied onto the skin of left auricle of the same mice (positive control; n=6). The thicknesses of right and left auricles were measured with a dial thickness gauge (OZAKI MFG. CO., LTD.) immediately before induction and 24, 48, and 72 hours after induction. The change in the auricular thickness relative to the thickness immediately before induction was used to assess the drug efficacy.

To assess the establishment of the pathological condition, a group in which ethanol-acetone mixed solution (3:1, v/v) without picryl chloride was applied onto the abdominal skin at the time of sensitization, and after five days 20 µL of 1% picryl chloride solution was applied onto the skin of right auricle and 20 µl of the solvent (acetone: olive=1:4, v/v) was applied onto the skin of left auricle, was studied as a control group (negative control group; n=6).

To assess the effect of administration of anti-NR10 antibody on the pathological condition in this model, a group in which acute contact dermatitis was elicited by the method used for the above positive control group and 10 mg/kg of BM095 was intravenously administered on the day before sensitization and the day before induction (BM095 group, n=6), and a group in which the vehicle (a mixture of acetate buffer (20 mmol/L sodium acetate, 20 mmol/L sodium chloride) and phosphate-buffered saline (PBS; GIBCO) at a volume ratio of 1:5) was administered at the same timing (vehicle group, n=5), were studied.

Figure 4:
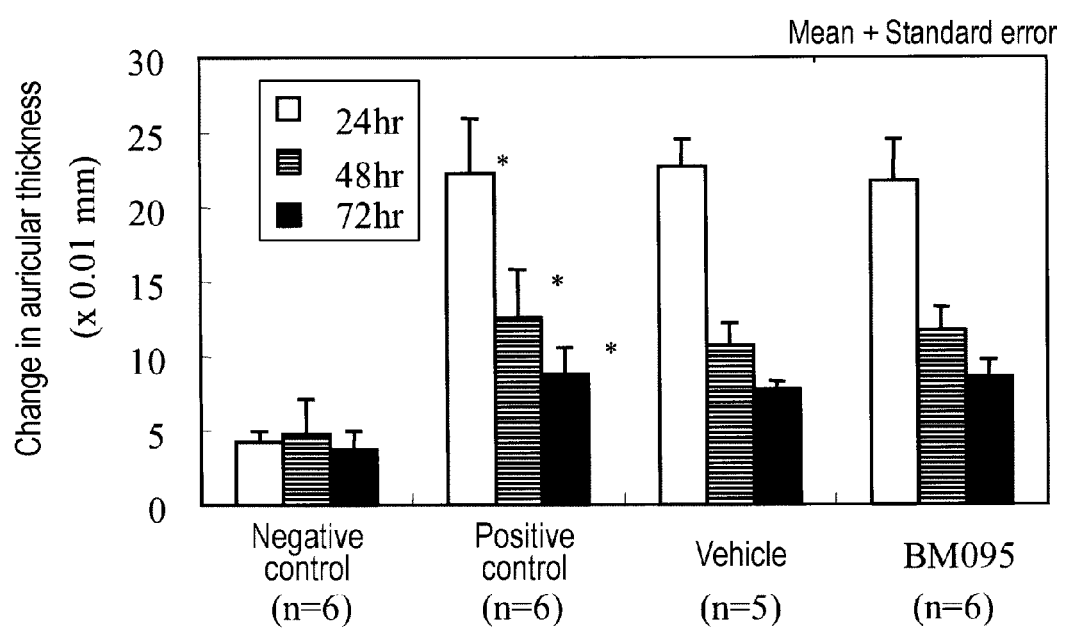
FIG. 4 is a graph showing the time course of changes in the auricular thickness in the picryl chloride-induced acute contact dermatitis model.

The time course of auricular thickness changes up to 72 hours after induction is shown in FIG. 4. Auricles were significantly thickened in the positive control group at all time points of 24, 48, and 72 hours after induction, as compared to the negative control group, showing the establishment of the pathological condition. In the meantime, the BM-095 group showed similar time course of auricular thickness changes to the vehicle group, and thus no significant suppression was observed.

These results revealed that BM095 administration had no therapeutic effect against acute contact dermatitis observed in this model.

INDUSTRIAL APPLICABILITY

NR10 antagonists, such as neutralizing antibodies against NR10, provided by the present invention are useful as therapeutic or preventive agents for pruritus.

The invention claimed is:

1. A method for suppressing or treating pruritus, which comprises administering a dose of an anti-NR10 (novel cytokine receptor 10) antibody having a neutralizing activity against NR10 to a patient in need thereof, thereby suppressing or treating pruritus, wherein the anti-NR10 antibody comprises a heavy chain with a variable region at least 85% identical to the variable region corresponding to amino acids 1 to 121 of SEQ ID NO: 17 and a light chain with a variable region at least 85% identical to the variable region corresponding to amino acids 1 to 107 of SEQ ID NO: 18.

2. The method of claim 1, wherein the antibody is a monoclonal antibody.

3. The method of claim 1, wherein the antibody is a recombinant antibody.

4. The method of claim 1, wherein the antibody is a chimeric, humanized, or human antibody.

5. The method of claim 2, wherein the NR10 is human NR10.

6. The method of claim 1, wherein the patient's pruritus is selected from the group consisting of pruritus in scabies, pediculation, bug bites and stings, urticaria, atopic dermatitis, contact dermatitis, lichen planus, miliaria, dermatitis herpetiformis, xeroderma, biliary obstruction, primary biliary cirrhosis (PBC), infectious hepatitis, uremia, chronic renal failure, renal dialysis, lymphoma, leukemia, polycythemia rubra vera, pregnancy, ingestion of drugs, hyperthyroidism, diabetes mellitus, and organ cancers.

7. The method of claim 1, wherein the anti-NR10 antibody recognizes a site within positions 21-120 of the amino acid sequence of SEQ ID NO:7.

8. The method of claim 1, wherein the anti-NR10 antibody comprises the heavy chain amino acid sequence of SEQ ID NO:17.

9. The method of claim 1, wherein the anti-NR10 antibody comprises the heavy chain amino acid sequence of SEQ ID NO:17 and the light chain amino acid sequence of SEQ ID NO:18.

10. The method of claim 1, wherein the anti-NR10 antibody comprises the heavy chain variable region corresponding to amino acids 1 to 121 of SEQ ID NO:17.

11. The method of claim 1, wherein the anti-NR10 antibody comprises the heavy chain variable region corresponding to amino acids 1 to 121 of SEQ ID NO:17 and the light chain variable region corresponding to amino acids 1 to 107 of SEQ ID NO:18.

12. The method of claim 1, wherein the anti-NR10 antibody comprises the heavy chain variable region corresponding to amino acids 1 to 121 of SEQ ID NO:17 with one amino acid substitution, deletion, or insertion.

13. The method of claim 1, wherein the anti-NR10 antibody comprises the heavy chain variable region corresponding to amino acids 1 to 121 of SEQ ID NO:17 with one amino acid substitution, deletion, or insertion and the light chain variable region corresponding to amino acids 1 to 107 of SEQ ID NO:18 with one amino acid substitution, deletion, or insertion.

14. The method of claim 1, wherein the anti-NR10 antibody comprises a heavy chain with a variable region at least 90% identical to the variable region corresponding to amino acids 1 to 121 of SEQ ID NO:17 or a light chain with a variable region at least 90% identical to the variable region corresponding to amino acids 1 to 107 of SEQ ID NO:18.

15. The method of claim 1, wherein the anti-NR10 antibody comprises a heavy chain with a variable region at least 95% identical to the variable region corresponding to amino acids 1 to 121 of SEQ ID NO:17 or a light chain with a variable region at least 95% identical to the variable region corresponding to amino acids 1 to 107 of SEQ ID NO:18.

16. The method of claim 1, wherein the anti-NR10 antibody comprises a heavy chain with a variable region at least 95% identical to the variable region corresponding to amino acids 1 to 121 of SEQ ID NO:17 and a light chain with a variable region at least 95% identical to the variable region corresponding to amino acids 1 to 107 of SEQ ID NO:18.

17. The method of claim 1, wherein the anti-NR10 antibody comprises complementarity determining regions (CDRs) 1-3 of SEQ ID NO:17, wherein CDR1 corresponds to amino acids 31 to 35 of SEQ ID NO:17, CDR2 corresponds to amino acids 50 to 66 of SEQ ID NO:17, and CDR3 corresponds to amino acids 99 to 110 of SEQ ID NO:17.

18. The method of claim 1, wherein the anti-NR10 antibody comprises CDRs 1-3 of SEQ ID NO:17, wherein CDR1 of SEQ ID NO:17 corresponds to amino acids 31 to 35, CDR2 of SEQ ID NO:17 corresponds to amino acids 50 to 66, and CDR3 of SEQ ID NO:17 corresponds to amino acids 99 to 110, and CDRs 1-3 of SEQ ID NO:18, wherein CDR1 of SEQ ID NO:18 corresponds to amino acids 24 to 34, CDR2 of SEQ ID NO:18 corresponds to amino acids 50 to 56, and CDR3 of SEQ ID NO:18 corresponds to amino acids 89 to 97.

19. The method of claim 1, wherein the anti-NR10 antibody is a scFv.

* * * * *

SEQUENCE LISTING

```
<160> NUMBER OF SEQ ID NOS: 18

<210> SEQ ID NO 1
<211> LENGTH: 125
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
```

```
                35                  40                  45
Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Asp Val Val Pro Ala Ala Met Ser Phe Tyr Tyr Gly Met
            100                 105                 110

Asp Val Trp Gly Arg Gly Thr Leu Val Thr Val Ser Ser
        115                 120                 125

<210> SEQ ID NO 2
<211> LENGTH: 375
<212> TYPE: DNA
<213> ORGANISM: Homo sapiens

<400> SEQUENCE: 2
caggtccagc tggtacagtc tggggctgag gtgaagaagc ctggggcctc agtgaaggtc     60
tcctgcaagg cttctggata caccttcacc ggctactata tgcactgggt gcgacaggcc    120
cctggacaag gcttgagtg gatgggatgg atcaaccctaa cagtggtgg cacaaactat    180 gcacagaagt tcagggcag gtcaccatg accaggaca cgtccatcag cacagcctac    240
atggagctga gcaggctgag atctgacgac acggccgtgt attactgtgc gagagaggac    300
gtagtaccag ctgctatgtc attctactac ggtatggacg tctggggccg aggaaccctg    360
gtcaccgtct cgagt                                                      375

<210> SEQ ID NO 3
<211> LENGTH: 109
<212> TYPE: PRT
<213> ORGANISM: Homo sapiens

<400> SEQUENCE: 3

Leu Pro Val Leu Thr Gln Pro Pro Ser Val Ser Val Ala Pro Gly Gln
  1               5                  10                  15

Thr Ala Arg Ile Thr Cys Gly Gly Asn Asn Ile Gly Ser Lys Thr Val
             20                  25                  30

Tyr Trp Tyr Gln Gln Glu Pro Gly Gln Ala Pro Val Leu Val Val Tyr
         35                  40                  45

Asp Asp Thr Asp Arg Pro Ala Gly Ile Pro Glu Arg Phe Ser Gly Ala
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Thr Asp His
                 85                  90                  95

Gly Val Phe Gly Gly Gly Thr Lys Leu Thr Val Leu Gly
            100                 105

<210> SEQ ID NO 4
<211> LENGTH: 327
<212> TYPE: DNA
<213> ORGANISM: Homo sapiens

<400> SEQUENCE: 4
ctgcctgtgc tgactcagcc cccctcggtg tcagtggccc caggacagac ggccaggatt     60
acctgtgggg gaaacaacat tggaagtaaa actgtgtact ggtaccagca ggagccaggc    120
```

```
caggcccctg tgttggtcgt ctatgatgat accgaccggc ccgcaggaat ccctgagcgc    180
ttctctggcg ccaactctgg gaacacggcc accctgacca tcagcagggt cgaagccggg    240
gatgaggccg actattactg tcaggtgtgg gatagtagta ctgatcatgg ggttttcggc    300
ggagggacca agctgaccgt cctaggt                                        327
```

```
<210> SEQ ID NO 5
<211> LENGTH: 716
<212> TYPE: PRT
<213> ORGANISM: Mus musculus

<400> SEQUENCE: 5

Met Trp Thr Leu Ala Leu Trp Ala Phe Ser Phe Leu Cys Lys Phe Ser
1               5                   10                  15

Leu Ala Val Leu Pro Thr Lys Pro Glu Asn Ile Ser Cys Val Phe Tyr
            20                  25                  30

Phe Asp Arg Asn Leu Thr Cys Thr Trp Arg Pro Glu Lys Glu Thr Asn
        35                  40                  45

Asp Thr Ser Tyr Ile Val Thr Leu Thr Tyr Ser Tyr Gly Lys Ser Asn
    50                  55                  60

Tyr Ser Asp Asn Ala Thr Glu Ala Ser Tyr Ser Phe Pro Arg Ser Cys
65                  70                  75                  80

Ala Met Pro Pro Asp Ile Cys Ser Val Glu Val Gln Ala Gln Asn Gly
                85                  90                  95

Asp Gly Lys Val Lys Ser Asp Ile Thr Tyr Trp His Leu Ile Ser Ile
            100                 105                 110

Ala Lys Thr Glu Pro Pro Ile Ile Leu Ser Val Asn Pro Ile Cys Asn
        115                 120                 125

Arg Met Phe Gln Ile Gln Trp Lys Pro Arg Glu Lys Thr Arg Gly Phe
    130                 135                 140

Pro Leu Val Cys Met Leu Arg Phe Arg Thr Val Asn Ser Ser Arg Trp
145                 150                 155                 160

Thr Glu Val Asn Phe Glu Asn Cys Lys Gln Val Cys Asn Leu Thr Gly
                165                 170                 175

Leu Gln Ala Phe Thr Glu Tyr Val Leu Ala Leu Arg Phe Arg Phe Asn
            180                 185                 190

Asp Ser Arg Tyr Trp Ser Lys Trp Ser Lys Glu Glu Thr Arg Val Thr
        195                 200                 205

Met Glu Glu Val Pro His Val Leu Asp Leu Trp Arg Ile Leu Glu Pro
    210                 215                 220

Ala Asp Met Asn Gly Asp Arg Lys Val Arg Leu Leu Trp Lys Lys Ala
225                 230                 235                 240

Arg Gly Ala Pro Val Leu Glu Lys Thr Phe Gly Tyr His Ile Gln Tyr
                245                 250                 255

Phe Ala Glu Asn Ser Thr Asn Leu Thr Glu Ile Asn Asn Ile Thr Thr
            260                 265                 270

Gln Gln Tyr Glu Leu Leu Leu Met Ser Gln Ala His Ser Val Ser Val
        275                 280                 285

Thr Ser Phe Asn Ser Leu Gly Lys Ser Gln Glu Ala Ile Leu Arg Ile
    290                 295                 300

Pro Asp Val His Glu Lys Thr Phe Gln Tyr Ile Lys Ser Met Lys Ala
305                 310                 315                 320

Tyr Ile Ala Glu Pro Leu Leu Val Val Asn Trp Gln Ser Ser Ile Pro
                325                 330                 335

Ala Val Asp Thr Trp Ile Val Glu Trp Leu Pro Glu Ala Ala Met Ser
```

```
                340             345             350
Lys Phe Pro Ala Leu Ser Trp Glu Ser Val Ser Gln Val Thr Asn Trp
            355                 360                 365

Thr Ile Glu Gln Asp Lys Leu Lys Pro Phe Thr Cys Tyr Asn Ile Ser
        370                 375                 380

Val Tyr Pro Val Leu Gly His Arg Val Gly Glu Pro Tyr Ser Ile Gln
385                 390                 395                 400

Ala Tyr Ala Lys Glu Gly Thr Pro Leu Lys Gly Pro Glu Thr Arg Val
                405                 410                 415

Glu Asn Ile Gly Leu Arg Thr Ala Thr Ile Thr Trp Lys Glu Ile Pro
            420                 425                 430

Lys Ser Ala Arg Asn Gly Phe Ile Asn Asn Tyr Thr Val Phe Tyr Gln
        435                 440                 445

Ala Glu Gly Gly Lys Glu Leu Ser Lys Thr Val Asn Ser His Ala Leu
    450                 455                 460

Gln Cys Asp Leu Glu Ser Leu Thr Arg Arg Thr Ser Tyr Thr Val Trp
465                 470                 475                 480

Val Met Ala Ser Thr Arg Ala Gly Gly Thr Asn Gly Val Arg Ile Asn
                485                 490                 495

Phe Lys Thr Leu Ser Ile Ser Val Phe Glu Ile Val Leu Leu Thr Ser
            500                 505                 510

Leu Val Gly Gly Gly Leu Leu Leu Ser Ile Lys Thr Val Thr Phe
        515                 520                 525

Gly Leu Arg Lys Pro Asn Arg Leu Thr Pro Leu Cys Cys Pro Asp Val
        530                 535                 540

Pro Asn Pro Ala Glu Ser Ser Leu Ala Thr Trp Leu Gly Asp Gly Phe
545                 550                 555                 560

Lys Lys Ser Asn Met Lys Glu Thr Gly Asn Ser Gly Asp Thr Glu Asp
                565                 570                 575

Val Val Leu Lys Pro Cys Pro Val Pro Ala Asp Leu Ile Asp Lys Leu
            580                 585                 590

Val Val Asn Phe Glu Asn Phe Leu Glu Val Val Leu Thr Glu Glu Ala
        595                 600                 605

Gly Lys Gly Gln Ala Ser Ile Leu Gly Gly Glu Ala Asn Glu Tyr Val
    610                 615                 620

Thr Ser Pro Ser Arg Pro Asp Gly Pro Pro Gly Lys Ser Phe Lys Glu
625                 630                 635                 640

Pro Ser Val Leu Thr Glu Val Ala Ser Glu Asp Ser His Ser Thr Cys
                645                 650                 655

Ser Arg Met Ala Asp Glu Ala Tyr Ser Glu Leu Ala Arg Gln Pro Ser
            660                 665                 670

Ser Ser Cys Gln Ser Pro Gly Leu Ser Pro Pro Arg Glu Asp Gln Ala
        675                 680                 685

Gln Asn Pro Tyr Leu Lys Asn Ser Val Thr Thr Arg Glu Phe Leu Val
    690                 695                 700

His Glu Asn Ile Pro Glu His Ser Lys Gly Glu Val
705                 710                 715

<210> SEQ ID NO 6
<211> LENGTH: 662
<212> TYPE: PRT
<213> ORGANISM: Homo sapiens

<400> SEQUENCE: 6

Met Lys Leu Ser Pro Gln Pro Ser Cys Val Asn Leu Gly Met Met Trp
```

```
              1               5                  10                 15
Thr Trp Ala Leu Trp Met Leu Pro Ser Leu Cys Lys Phe Ser Leu Ala
                20              25              30

Ala Leu Pro Ala Lys Pro Glu Asn Ile Ser Cys Val Tyr Tyr Tyr Arg
            35              40                  45

Lys Asn Leu Thr Cys Thr Trp Ser Pro Gly Lys Glu Thr Ser Tyr Thr
        50              55              60

Gln Tyr Thr Val Lys Arg Thr Tyr Ala Phe Gly Glu Lys His Asp Asn
65                  70              75                      80

Cys Thr Thr Asn Ser Ser Thr Ser Glu Asn Arg Ala Ser Cys Ser Phe
                85              90              95

Phe Leu Pro Arg Ile Thr Ile Pro Asp Asn Tyr Thr Ile Glu Val Glu
            100             105             110

Ala Glu Asn Gly Asp Gly Val Ile Lys Ser His Met Thr Tyr Trp Arg
            115             120             125

Leu Glu Asn Ile Ala Lys Thr Glu Pro Pro Lys Ile Phe Arg Val Lys
            130             135             140

Pro Val Leu Gly Ile Lys Arg Met Ile Gln Ile Glu Trp Ile Lys Pro
145             150             155                         160

Glu Leu Ala Pro Val Ser Ser Asp Leu Lys Tyr Thr Leu Arg Phe Arg
                165             170             175

Thr Val Asn Ser Thr Ser Trp Met Glu Val Asn Phe Ala Lys Asn Arg
            180             185             190

Lys Asp Lys Asn Gln Thr Tyr Asn Leu Thr Gly Leu Gln Pro Phe Thr
            195             200             205

Glu Tyr Val Ile Ala Leu Arg Cys Ala Val Lys Glu Ser Lys Phe Trp
            210             215             220

Ser Asp Trp Ser Gln Glu Lys Met Gly Met Thr Glu Glu Ala Pro
225             230             235                         240

Cys Gly Leu Glu Leu Trp Arg Val Leu Lys Pro Ala Glu Ala Asp Gly
            245             250             255

Arg Arg Pro Val Arg Leu Leu Trp Lys Lys Ala Arg Gly Ala Pro Val
            260             265             270

Leu Glu Lys Thr Leu Gly Tyr Asn Ile Trp Tyr Tyr Pro Glu Ser Asn
            275             280             285

Thr Asn Leu Thr Glu Thr Met Asn Thr Thr Asn Gln Gln Leu Glu Leu
            290             295             300

His Leu Gly Gly Glu Ser Phe Trp Val Ser Met Ile Ser Tyr Asn Ser
305             310             315                         320

Leu Gly Lys Ser Pro Val Ala Thr Leu Arg Ile Pro Ala Ile Gln Glu
            325             330             335

Lys Ser Phe Gln Cys Ile Glu Val Met Gln Ala Cys Val Ala Glu Asp
            340             345             350

Gln Leu Val Val Lys Trp Gln Ser Ser Ala Leu Asp Val Asn Thr Trp
            355             360             365

Met Ile Glu Trp Phe Pro Asp Val Asp Ser Glu Pro Thr Thr Leu Ser
            370             375             380

Trp Glu Ser Val Ser Gln Ala Thr Asn Trp Thr Ile Gln Gln Asp Lys
385             390             395                         400

Leu Lys Pro Phe Trp Cys Tyr Asn Ile Ser Val Tyr Pro Met Leu His
            405             410             415

Asp Lys Val Gly Glu Pro Tyr Ser Ile Gln Ala Tyr Ala Lys Glu Gly
            420             425             430
```

```
Val Pro Ser Glu Gly Pro Glu Thr Lys Val Glu Asn Ile Gly Val Lys
        435                 440                 445

Thr Val Thr Ile Thr Trp Lys Glu Ile Pro Lys Ser Glu Arg Lys Gly
        450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
            485                 490                 495

Leu Lys Arg Lys Thr Ser Tyr Ile Val Gln Val Met Ala Ser Thr Ser
        500                 505                 510

Ala Gly Gly Thr Asn Gly Thr Ser Ile Asn Phe Lys Thr Leu Ser Phe
        515                 520                 525

Ser Val Phe Glu Ile Ile Leu Ile Thr Ser Leu Ile Gly Gly Gly Leu
        530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
            565                 570                 575

Ser Ile Ala Thr Trp His Gly Asp Asp Phe Lys Asp Lys Leu Asn Leu
        580                 585                 590

Lys Glu Ser Asp Asp Ser Val Asn Thr Glu Asp Arg Ile Leu Lys Pro
        595                 600                 605

Cys Ser Thr Pro Ser Asp Lys Leu Val Ile Asp Lys Leu Val Val Asn
610                 615                 620

Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
            645                 650                 655

Ser Cys Pro Thr Ser Ile
            660

<210> SEQ ID NO 7
<211> LENGTH: 732
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: TRANSMEM
<222> LOCATION: (520)..(543)

<400> SEQUENCE: 7

Met Met Trp Thr Trp Ala Leu Trp Met Leu Pro Ser Leu Cys Lys Phe
1               5                   10                  15

Ser Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Val Lys Arg Thr Tyr Ala Phe Gly Glu Lys
    50                  55                  60

His Asp Asn Cys Thr Thr Asn Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser His Met Thr
            100                 105                 110
```

-continued

Tyr Trp Arg Leu Glu Asn Ile Ala Lys Thr Glu Pro Pro Lys Ile Phe
            115                 120                 125

Arg Val Lys Pro Val Leu Gly Ile Lys Arg Met Ile Gln Ile Glu Trp
130                 135                 140

Ile Lys Pro Glu Leu Ala Pro Val Ser Ser Asp Leu Lys Tyr Thr Leu
145                 150                 155                 160

Arg Phe Arg Thr Val Asn Ser Thr Ser Trp Met Glu Val Asn Phe Ala
                165                 170                 175

Lys Asn Arg Lys Asp Lys Asn Gln Thr Tyr Asn Leu Thr Gly Leu Gln
            180                 185                 190

Pro Phe Thr Glu Tyr Val Ile Ala Leu Arg Cys Ala Val Lys Glu Ser
            195                 200                 205

Lys Phe Trp Ser Asp Trp Ser Gln Glu Lys Met Gly Met Thr Glu Glu
210                 215                 220

Glu Ala Pro Cys Gly Leu Glu Leu Trp Arg Val Leu Lys Pro Ala Glu
225                 230                 235                 240

Ala Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Tyr Pro
            260                 265                 270

Glu Ser Asn Thr Asn Leu Thr Glu Thr Met Asn Thr Thr Asn Gln Gln
            275                 280                 285

Leu Glu Leu His Leu Gly Gly Glu Ser Phe Trp Val Ser Met Ile Ser
            290                 295                 300

Tyr Asn Ser Leu Gly Lys Ser Pro Val Ala Thr Leu Arg Ile Pro Ala
305                 310                 315                 320

Ile Gln Glu Lys Ser Phe Gln Cys Ile Glu Val Met Gln Ala Cys Val
                325                 330                 335

Ala Glu Asp Gln Leu Val Val Lys Trp Gln Ser Ser Ala Leu Asp Val
            340                 345                 350

Asn Thr Trp Met Ile Glu Trp Phe Pro Asp Val Asp Ser Glu Pro Thr
            355                 360                 365

Thr Leu Ser Trp Glu Ser Val Ser Gln Ala Thr Asn Trp Thr Ile Gln
370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Val Pro Ser Glu Gly Pro Glu Thr Lys Val Glu Asn Ile
            420                 425                 430

Gly Val Lys Thr Val Thr Ile Thr Trp Lys Glu Ile Pro Lys Ser Glu
            435                 440                 445

Arg Lys Gly Ile Ile Cys Asn Tyr Thr Ile Phe Tyr Gln Ala Glu Gly
450                 455                 460

Gly Lys Gly Phe Ser Lys Thr Val Asn Ser Ser Ile Leu Gln Tyr Gly
465                 470                 475                 480

Leu Glu Ser Leu Lys Arg Lys Thr Ser Tyr Ile Val Gln Val Met Ala
                485                 490                 495

Ser Thr Ser Ala Gly Gly Thr Asn Gly Thr Ser Ile Asn Phe Lys Thr
            500                 505                 510

Leu Ser Phe Ser Val Phe Glu Ile Ile Leu Ile Thr Ser Leu Ile Gly
            515                 520                 525

Gly Gly Leu Leu Ile Leu Ile Ile Leu Thr Val Ala Tyr Gly Leu Lys
530                 535                 540

```
Lys Pro Asn Lys Leu Thr His Leu Cys Trp Pro Thr Val Pro Asn Pro
545                 550                 555                 560

Ala Glu Ser Ser Ile Ala Thr Trp His Gly Asp Asp Phe Lys Asp Lys
            565                 570                 575

Leu Asn Leu Lys Glu Ser Asp Asp Ser Val Asn Thr Glu Asp Arg Ile
        580                 585                 590

Leu Lys Pro Cys Ser Thr Pro Ser Asp Lys Leu Val Ile Asp Lys Leu
    595                 600                 605

Val Val Asn Phe Gly Asn Val Leu Gln Glu Ile Phe Thr Asp Glu Ala
610                 615                 620

Arg Thr Gly Gln Glu Asn Asn Leu Gly Gly Glu Lys Asn Gly Tyr Val
625                 630                 635                 640

Thr Cys Pro Phe Arg Pro Asp Cys Pro Leu Gly Lys Ser Phe Glu Glu
            645                 650                 655

Leu Pro Val Ser Pro Glu Ile Pro Pro Arg Lys Ser Gln Tyr Leu Arg
            660                 665                 670

Ser Arg Met Pro Glu Gly Thr Arg Pro Glu Ala Lys Glu Gln Leu Leu
        675                 680                 685

Phe Ser Gly Gln Ser Leu Val Pro Asp His Leu Cys Glu Glu Gly Ala
690                 695                 700

Pro Asn Pro Tyr Leu Lys Asn Ser Val Thr Ala Arg Glu Phe Leu Val
705                 710                 715                 720

Ser Glu Lys Leu Pro Glu His Thr Lys Gly Glu Val
                725                 730

<210> SEQ ID NO 8
<211> LENGTH: 4
<212> TYPE: PRT
<213> ORGANISM: Artificial
<220> FEATURE:
<223> OTHER INFORMATION: An artificially synthesized peptide sequence

<400> SEQUENCE: 8

Gly Gly Gly Ser
1

<210> SEQ ID NO 9
<211> LENGTH: 4
<212> TYPE: PRT
<213> ORGANISM: Artificial
<220> FEATURE:
<223> OTHER INFORMATION: An artificially synthesized peptide sequence

<400> SEQUENCE: 9

Ser Gly Gly Gly
1

<210> SEQ ID NO 10
<211> LENGTH: 5
<212> TYPE: PRT
<213> ORGANISM: Artificial
<220> FEATURE:
<223> OTHER INFORMATION: An artificially synthesized peptide sequence

<400> SEQUENCE: 10

Gly Gly Gly Gly Ser
1               5

<210> SEQ ID NO 11
<211> LENGTH: 5
<212> TYPE: PRT
```

-continued

```
<213> ORGANISM: Artificial
<220> FEATURE:
<223> OTHER INFORMATION: An artificially synthesized peptide sequence

<400> SEQUENCE: 11

Ser Gly Gly Gly Gly
1               5

<210> SEQ ID NO 12
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 12

Gly Gly Gly Gly Gly Ser
1               5

<210> SEQ ID NO 13
<211> LENGTH: 6
<212> TYPE: PRT
<213> ORGANISM: Artificial
<220> FEATURE:
<223> OTHER INFORMATION: An artificially synthesized peptide sequence

<400> SEQUENCE: 13

Ser Gly Gly Gly Gly Gly
1               5

<210> SEQ ID NO 14
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 14

Gly Gly Gly Gly Gly Gly Ser
1               5

<210> SEQ ID NO 15
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 15

Ser Gly Gly Gly Gly Gly Gly
1               5

<210> SEQ ID NO 16
<211> LENGTH: 2969
<212> TYPE: DNA
<213> ORGANISM: Homo sapiens

<400> SEQUENCE: 16
cgcttataaa tgaatgtgtg cttaggaaca ccagacagca ctccagcact ctgcttgggg      60
ggcattcgaa acagcaaaat cactcataaa aggcaaaaaa ttgcaaaaaa aatagtaata     120
accagcatgg tactaaatag accatgaaaa gacatgtgtg tgcagtatga aaattgagac     180
aggaaggcag agtgtcagct tgttccacct cagctgggaa tgtgcatcag gcaactcaag     240 ttttcacca cggcatgtgt ctgtgaatgt ccgcaaaaca ttttaacaat aatgcaatcc      300
atttcccagc ataagtgggt aagtgccact ttgacttggg ctgggcttaa aagcacaaga     360
```

```
aaagctcgca gacaatcaga gtggaaacac tcccacatct tagtgtggat aaattaaagt    420
ccagattgtt cttcctgtcc tgacttgtgc tgtgggaggt ggagttgcct ttgatgcaaa    480
tcctttgagc cagcagaaca tctgtggaac atcccctgat acatgaagct ctctccccag    540
ccttcatgtg ttaacctggg gatgatgtgg acctgggcac tgtggatgct cccctcactc    600
tgcaaattca gcctggcagc tctgccagct aagcctgaga acatttcctg tgtctactac    660
tataggaaaa atttaacctg cacttggagt ccaggaaagg aaaccagtta tacccagtac    720
acagttaaga gaacttacgc tttcggagaa aaacatgata attgtacaac caatagttct    780
acaagtgaaa atcgtgcttc gtgctctttt ttccttccaa gaataacgat cccagataat    840
tataccattg aggtggaagc tgaaaatgga gatggtgtaa ttaaatctca tatgacatac    900
tggagattag agaacatagc gaaaactgaa ccacctaaga ttttccgtgt gaaaccagtt    960
ttgggcatca aacgaatgat tcaaattgaa tggataaagc ctgagttggc gcctgtttca   1020
tctgatttaa aatacacact tcgattcagg acagtcaaca gtaccagctg gatggaagtc   1080
aacttcgcta agaaccgtaa ggataaaaac caaacgtaca acctcacggg gctgcagcct   1140
tttacagaat atgtcatagc tctgcgatgt gcggtcaagg agtcaaagtt ctggagtgac   1200
tggagccaag aaaaaatggg aatgactgag gaagaagctc catgtggcct ggaactgtgg   1260
agagtcctga aaccagctga ggcggatgga agaaggccag tgcggttgtt atggaagaag   1320
gcaagaggag ccccagtcct agagaaaaca cttggctaca acatatggta ctatccagaa   1380
agcaacacta acctcacaga aacaatgaac actactaacc agcagcttga actgcatctg   1440
ggaggcgaga gcttttgggt gtctatgatt tcttataatt ctcttgggaa gtctccagtg   1500
gccaccctga ggattccagc tattcaagaa aaatcatttc agtgcattga ggtcatgcag   1560
gcctgcgttg ctgaggacca gctagtggtg aagtggcaaa gctctgctct agacgtgaac   1620
acttggatga ttgaatggtt tccggatgtg gactcagagc ccaccaccct ttcctgggaa   1680
tctgtgtctc aggccacgaa ctggacgatc cagcaagata aattaaaacc tttctggtgc   1740
tataacatct ctgtgtatcc aatgttgcat gacaaagttg gcgagccata ttccatccag   1800
gcttatgcca aagaaggcgt tccatcagaa ggtcctgaga ccaaggtgga gaacattggc   1860
gtgaagacgg tcacgatcac atggaaagag attcccaaga gtgagagaaa gggtatcatc   1920
tgcaactaca ccatctttta ccaagctgaa ggtggaaaag gattctccaa gacagtcaat   1980
tccagcatct tgcagtacgg cctggagtcc ctgaaacgaa agacctctta cattgttcag   2040
gtcatggcca acaccagtgc tggggggaacc aacgggacca gcataaattt caagacattg   2100
tcattcagtg tctttgagat tatcctcata acttctctga ttggtggagg ccttcttatt   2160
ctcattatcc tgacagtggc atatggtctc aaaaaaccca acaaattgac tcatctgtgt   2220
tggcccaccg ttcccaaccc tgctgaaagt agtatagcca catggcatgg agatgatttc   2280
aaggataagc taaacctgaa ggagtctgat gactctgtga acacagaaga caggatctta   2340
aaaccatgtt ccaccccccag tgacaagttg tgtgattgaca agttggtggt gaactttggg   2400
aatgttctgc aagaaatttt cacagatgaa gccagaacgg gtcaggaaaa acaatttagg   2460
agggaaaaag aatgggacta gaattctgtc ttcctgccca acttcaatat aagtgtggac   2520
taaaatgcga gaaggtgtc ctgtggtcta tgcaaattag aaaggacatg cagagttttc    2580
caactaggaa gactgaatct gtggccccaa gagaaccatc tccgaagact gggtatgtgg   2640
tcttttccac acatggacca cctacggatg caatctgtaa tgcatgtgca tgagaagtct   2700
gttattaagt agagtgtgaa aacatggtta tggtaatagg aacagctttt aaaatgcttt   2760
```

```
tgtatttggg cctttcacac aaaaaagcca taataccatt ttcatgtaat gctatacttc    2820
tatactattt tcatgtaata ctatacttct atactatttt catgtaatac tatacttcta    2880
tactattttc atgtaatact atacttctat attaaagttt tacccactcc aaaaaaagaa    2940
aaaaaaaaaa aaaaaaaaaa aaaaaaaaa                                      2969
```

<210> SEQ ID NO 17
<211> LENGTH: 447
<212> TYPE: PRT
<213> ORGANISM: Artificial
<220> FEATURE:
<223> OTHER INFORMATION: an artificially synthesized sequence

<400> SEQUENCE: 17

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
```

```
                325                 330                 335
Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 18
<211> LENGTH: 214
<212> TYPE: PRT
<213> ORGANISM: Artificial
<220> FEATURE:
<223> OTHER INFORMATION: an artificially synthesized sequence

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Phe
            20                  25                  30

Leu Ala Trp Tyr Gln Gln Lys Pro Gly Lys Ala Pro Lys Leu Leu Ile
            35                  40                  45

Tyr Asn Ala Lys Thr Leu Ala Lys Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
            85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210
```